US011198628B2

(12) United States Patent
Sassow

(10) Patent No.: US 11,198,628 B2
(45) Date of Patent: *Dec. 14, 2021

(54) MODULAR PORTABLE RENEWABLE ENERGY MICROGENERATION SYSTEM

(71) Applicant: SEaB Power Limited, London (GB)

(72) Inventor: Nicolas W. Sassow, Winchester (GB)

(73) Assignee: SEAB POWER LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/831,309

(22) Filed: Mar. 26, 2020

(65) Prior Publication Data

US 2020/0223726 A1    Jul. 16, 2020

Related U.S. Application Data

(63) Continuation of application No. 16/220,490, filed on Dec. 14, 2018, now Pat. No. 10,611,655.
(Continued)

(51) Int. Cl.
*C02F 3/28* (2006.01)
*C02F 11/04* (2006.01)
(Continued)

(52) U.S. Cl.
CPC .......... *C02F 3/2893* (2013.01); *C02F 3/006* (2013.01); *C02F 9/005* (2013.01); *C02F 11/04* (2013.01);
(Continued)

(58) Field of Classification Search
CPC ........ C02F 3/2893; C02F 11/04; C02F 3/006; C02F 9/005; C02F 1/441; C02F 11/125;
(Continued)

(56) References Cited

U.S. PATENT DOCUMENTS

| 3,342,727 A | 9/1967 | Bringle |
| 4,246,099 A | 4/1981 | Gould et al. |

(Continued)

FOREIGN PATENT DOCUMENTS

| AT | 004680 U1 | 10/2001 |
| BE | 1017711 A6 | 4/2009 |

(Continued)

OTHER PUBLICATIONS

Portaferm Small Manure Biogas Plant, available at http://www.portaferm-biogas.de/entwicklung_en.html (11 pages); Publication Date Unknown.

(Continued)

*Primary Examiner* — Fred Prince
(74) *Attorney, Agent, or Firm* — Baker Botts L.L.P.

(57) ABSTRACT

A portable and modular renewable energy microgeneration apparatus is disclosed that includes at least four modular units. The first modular unit includes a mixing tank and a chopper. The second modular unit includes a buffer tank, a liquor tank, and a pasteurization tank that pasteurizes waste that has been mixed with liquid from the liquor tank by the mixer, chopped into smaller sized components by the chopper, and pre-warmed by the buffer tank. The third modular unit includes a digestion tank that performs anaerobic digestion on pasteurized waste received from the pasteurization tank. And the fourth modular unit includes a gas storage tank that stores gas generated by the waste in at least one of the mixing tank, the chopper, the buffer tank, the liquor tank, the pasteurization tank, and the digestion tank. Each of the four modular units is both portable and modular.

10 Claims, 20 Drawing Sheets

Related U.S. Application Data

(60) Provisional application No. 62/620,608, filed on Jan. 23, 2018, provisional application No. 62/599,359, filed on Dec. 15, 2017.

(51) Int. Cl.

| | |
|---|---|
| *C02F 3/00* | (2006.01) |
| *C05F 11/00* | (2006.01) |
| *C05F 17/20* | (2020.01) |
| *C05F 17/50* | (2020.01) |
| *C05G 3/40* | (2020.01) |
| *C02F 9/00* | (2006.01) |
| *C02F 1/44* | (2006.01) |
| *C02F 11/12* | (2019.01) |
| *C05F 9/00* | (2006.01) |
| *C02F 11/18* | (2006.01) |
| *C12M 3/00* | (2006.01) |
| *C12M 1/00* | (2006.01) |
| *C12M 1/34* | (2006.01) |
| *C12M 1/107* | (2006.01) |
| *C05F 17/914* | (2020.01) |
| *C05F 17/964* | (2020.01) |
| *C05F 17/10* | (2020.01) |
| *C02F 11/125* | (2019.01) |
| *C02F 103/32* | (2006.01) |

(52) U.S. Cl.
CPC .............. *C05F 11/00* (2013.01); *C05F 17/10* (2020.01); *C05F 17/15* (2020.01); *C05F 17/20* (2020.01); *C05F 17/50* (2020.01); *C05F 17/914* (2020.01); *C05F 17/964* (2020.01); *C05G 3/40* (2020.02); *C05G 3/44* (2020.02); *C12M 21/04* (2013.01); *C12M 23/36* (2013.01); *C12M 23/44* (2013.01); *C12M 23/52* (2013.01); *C12M 41/26* (2013.01); *C12M 41/34* (2013.01); *C12M 43/08* (2013.01); *C12M 45/20* (2013.01); *C02F 1/441* (2013.01); *C02F 9/00* (2013.01); *C02F 11/125* (2013.01); *C02F 11/185* (2013.01); *C02F 2103/32* (2013.01); *C02F 2201/007* (2013.01); *C02F 2201/008* (2013.01); *C02F 2209/006* (2013.01); *C02F 2209/05* (2013.01); *C02F 2209/285* (2013.01); *C02F 2301/046* (2013.01); *C02F 2301/08* (2013.01); *C02F 2303/02* (2013.01); *C02F 2303/10* (2013.01); *C05F 9/00* (2013.01); *C12M 23/00* (2013.01); *C12M 23/58* (2013.01)

(58) Field of Classification Search
CPC ............ C02F 2301/046; C02F 2209/05; C02F 2209/006; C02F 2209/285; C02F 11/185; C02F 9/00; C02F 2201/007; C02F 2201/008; C02F 2103/32; C02F 2301/08; C02F 2303/02; C02F 2303/10; C05F 17/15; C05F 17/10; C05F 17/20; C05F 17/50; C05F 17/914; C05F 17/964; C05F 11/00; C05F 9/00; C05G 3/40; C05G 3/44; C12M 23/44; C12M 23/52; C12M 41/34; C12M 43/08; C12M 41/26; C12M 21/04; C12M 45/20; C12M 23/36; C12M 23/58; C12M 23/00; Y02E 50/30; Y02W 30/40; Y02W 10/20; Y02W 10/30; Y02W 10/37; Y02A 20/131; Y02P 20/133; Y02P 20/145; Y02P 20/59

USPC ....... 210/603, 609, 614, 173, 252, 259, 260, 210/916, 175
See application file for complete search history.

(56) References Cited

U.S. PATENT DOCUMENTS

| | | |
|---|---|---|
| 5,121,600 A | 6/1992 | Sanders et al. |
| 5,158,593 A | 10/1992 | DeLima |
| 6,015,496 A | 1/2000 | Khudenko |
| 6,786,051 B2 | 9/2004 | Kristich et al. |
| 6,905,600 B2 | 6/2005 | Lee, Jr. |
| 7,169,821 B2 | 1/2007 | Branson |
| 7,635,587 B2 | 12/2009 | Pearce, III et al. |
| 7,753,972 B2 | 7/2010 | Zubrin et al. |
| 8,092,680 B2 | 1/2012 | Johnson |
| 9,272,930 B2 | 3/2016 | Sassow |
| 2003/0082796 A1 | 5/2003 | Brown et al. |
| 2004/0154982 A1 | 8/2004 | Irani |
| 2007/0006528 A1 | 1/2007 | Diebold et al. |
| 2007/0221552 A1 | 9/2007 | Denney |
| 2009/0013601 A1 | 1/2009 | Mandich et al. |
| 2010/0155313 A1 | 6/2010 | Wilson et al. |
| 2010/0281759 A1 | 11/2010 | Yanik et al. |
| 2011/0003357 A1 | 1/2011 | Barclay et al. |
| 2011/0200954 A1 | 8/2011 | Sassow |
| 2011/0203992 A1 | 8/2011 | Liu et al. |
| 2013/0020257 A1 | 1/2013 | McCarty |
| 2016/0083683 A1 | 3/2016 | Augustine et al. |
| 2019/0016960 A1* | 1/2019 | Griffiths .................. C10B 49/10 |

FOREIGN PATENT DOCUMENTS

| | | |
|---|---|---|
| CN | 104903015 A | 9/2015 |
| DE | 8909229 U1 | 11/1989 |
| DE | 19833624 A1 | 1/2000 |
| DE | 19958142 A1 | 2/2001 |
| DE | 20016591 U1 | 2/2001 |
| DE | 202006013772 U1 | 11/2006 |
| DE | 102010044988 A1 | 3/2012 |
| EP | 1475354 A1 | 11/2004 |
| JP | 2003-184575 A | 7/2003 |
| WO | 93/04988 A1 | 3/1993 |
| WO | 2009/055793 A1 | 4/2009 |

OTHER PUBLICATIONS

Pietschmann, T., et al., "Portaferm—A Portable Hydrolysis Unit for Anaerobic Digestion Systems," Portaferm, Bauhaus-Universitat Weimar, Germany (11 pages); Publication Date Unknown.
United Kingdom Intellectual Property Office, Office Communication for British Patent Application No. GB 1203901.2 (counterpart to co-pending U.S. Appl. No. 13/085,320), dated Mar. 22, 2012.
Intellectual Property Office of the United Kingdom, Office Action for British Patent Application No. GB1203901.2 (counterpart British patent application), dated Dec. 14, 2012.
European Patent Office, Written Opinion of the International Searching Authority for International Patent Application No. PCT/IB2011/001279 (counterpart International patent application), dated Oct. 31, 2011.
European Patent Office, Office Action for European Patent Application No. 11748711.6 (counterpart European patent application), dated Jun. 15, 2012.
Ecovation MFTsm Pilot Program; Mobile High-Rate Anaerobic Treatment; Ecovation, Inc.; Sent May 13, 2008.
European Patent Office, International Search Report issued in International Application No. PCT/IB2018/060064, dated Mar. 19, 2019.
European Patent Office, Written Opinion of the International Searching Authority issued in International Application No. PCT/IB2018/060064, dated Mar. 19, 2019.

* cited by examiner

MODULAR PORTABLE RENEWABLE ENERGY MICROGENERATION SYSTEM

CROSS-REFERENCE TO RELATED APPLICATIONS

The present application is a continuation of U.S. application Ser. No. 16/220,490, filed Dec. 14, 2018, which claims the benefit of U.S. provisional application Ser. Nos. 62/599,359, filed Dec. 15, 2017, and 62/620,608, filed Jan. 23, 2018. The present application also is related to currently-pending U.S. application Ser. No. 15/596,479, filed May 16, 2017, which is a continuation of U.S. application Ser. No. 14/995,407, filed Jan. 14, 2016, now U.S. Pat. No. 9,682,880, which is a continuation of U.S. application Ser. No. 13/910,682, filed Jun. 5, 2013, now U.S. Pat. No. 9,272,930, which is a continuation of U.S. application Ser. No. 13/526,024, filed Jun. 18, 2012, now U.S. Pat. No. 8,465,645, which is a continuation of U.S. application Ser. No. 13/085,320, filed Apr. 12, 2011, now U.S. Pat. No. 8,221,626, which claims the benefit of U.S. Provisional Application Ser. No. 61/323,186, filed Apr. 12, 2010, and U.S. Provisional Application Ser. No. 61/348,689, filed May 26, 2010. The disclosures of those patents and patent applications are hereby incorporated in their entirety by reference as if fully set forth herein.

FIELD OF THE INVENTION

The present invention relates to an improved method and device for providing renewable energy and making users less dependent on local utility providers by recycling their organic waste onsite. More particularly, the present invention relates to improvements to an anaerobic digester that allows users to convert organic waste into sustainable energy.

BACKGROUND OF THE INVENTION

There is a need in the art for a renewable energy microgeneration system in a single, modular, portable configuration that will allow users to convert organic waste into sustainable energy onsite. There also is a need in the art for a renewable energy microgeneration system with a reduced footprint, with separate containers for its different components, with modular interconnectivity between those containers, and with increased throughput.

SUMMARY OF THE INVENTION

To address at least the problems and/or disadvantages described above, it is a non-limiting object of the present invention to provide a portable and modular renewable energy microgeneration apparatus. The renewable energy microgeneration apparatus includes a first modular unit, a second modular unit, a third modular unit, and fourth modular unit. The first modular unit, the second modular unit, the third modular unit, and the fourth modular unit are portable in that they are configured to be transported to a site and placed in fluid communication with each other at the site. The first modular unit, the second modular unit, the third modular unit, and the fourth modular unit also are modular in that they can be combined with each other in different numbers and configurations.

The first modular unit includes a mixing tank that is configured to mix waste with a liquid and a chopper in fluid communication with the mixing tank that is configured to reduce the waste to smaller sized components. The second modular unit includes a buffer tank configured to receive the waste from the first modular unit and pre-warm the waste in preparation for pasteurization and a plurality of first holding tanks that are configured to receive the waste from the buffer tank and perform pasteurization on the waste. The third modular unit includes one or more second holding tanks that are configured to perform anaerobic digestion on the waste, each of the one or more second holding tanks being larger in volume than each of the plurality of first holding tanks. And the fourth modular unit includes one or more third holding tanks that are configured to store gas generated by the waste in at least one of the mixing tank, the chopper, the buffer tank, the plurality of first holding tanks, the one or more second holding tanks, and the one or more third holding tanks. Each of the mixing tank, the chopper, the buffer tank, the plurality of first holding tanks, and the one or more third holding tanks is sized to support anaerobic digestion in a plurality of third modular units.

In certain embodiments, the second modular unit further includes a liquor tank configured to store liquid that is removed from the waste after anaerobic digestion is performed on the waste. In addition, the renewable energy microgeneration apparatus may further include a fifth modular unit, the fifth modular unit comprising a de-watering device that is configured to separate what remains of the waste after anaerobic digestion is performed into solid waste and liquid waste, wherein the fifth modular device is portable and modular in the same manner as the first modular unit, the second modular unit, the third modular unit, and the fourth modular unit. The fifth modular unit also may include a salt removal system configured to remove salt from the liquid waste output by the de-watering device. The fifth modular unit also may include a bagging system configured to place solid waste output by the de-watering device into standard sized containers.

Also in certain embodiments, renewable energy microgeneration apparatus may include an odor management system configured to remove gas from within at least one of the first modular unit, the second modular unit, and the third modular unit; filter odors from the gas removed from the first modular unit, the second modular unit, and the third modular unit; and vent to atmosphere the gas removed from the first modular unit, the second modular unit, and the third modular unit, wherein the gas removed from the first modular unit, the second modular unit, and the third modular unit differs from the gas generated by the waste in at least one of the mixing tank, the chopper, the buffer tank, the plurality of first holding tanks, the one or more second holding tanks, and the one or more third holding tanks. The renewable energy microgeneration apparatus also may include a $CO_2$ extraction system configured to separate $CO_2$ from the gas generated by the waste in at least one of the mixing tank, the chopper, the buffer tank, the plurality of first holding tanks, the one or more second holding tanks, and the one or more third holding tanks; and inject the $CO_2$ into the one or more second holding tanks to stir the waste in the one or more second holding tanks.

In addition, each of the first modular unit, the second modular unit, the third modular unit, and the fourth modular unit may be disposed in a portable container, with each container being configured to withstand explosions of a predetermined magnitude without compromising an adjacent container. The first modular unit, the second modular unit, the third modular unit, and the fourth modular unit may be combined with each other in different numbers and configurations using piping and wiring disposed within the portable container of each of the first modular unit, the second modular unit, the third modular unit, and the fourth modular unit; and the piping and wiring are configured to be connected and disconnected via connection points housed within the portable container of each of the first modular unit, the second modular unit, the third modular unit, and the fourth modular unit. Furthermore, the renewable energy microgeneration apparatus may include a natural gas boiling configured to generate at least of electricity and heat from the gas removed from the at least one of first modular unit, the second modular unit, and the third modular unit.

BRIEF DESCRIPTION OF THE DRAWINGS

Aspects of the present invention can be better understood with reference to the following drawings, which are part of the specification and represent preferred embodiments of the present invention.

Figure 1A:
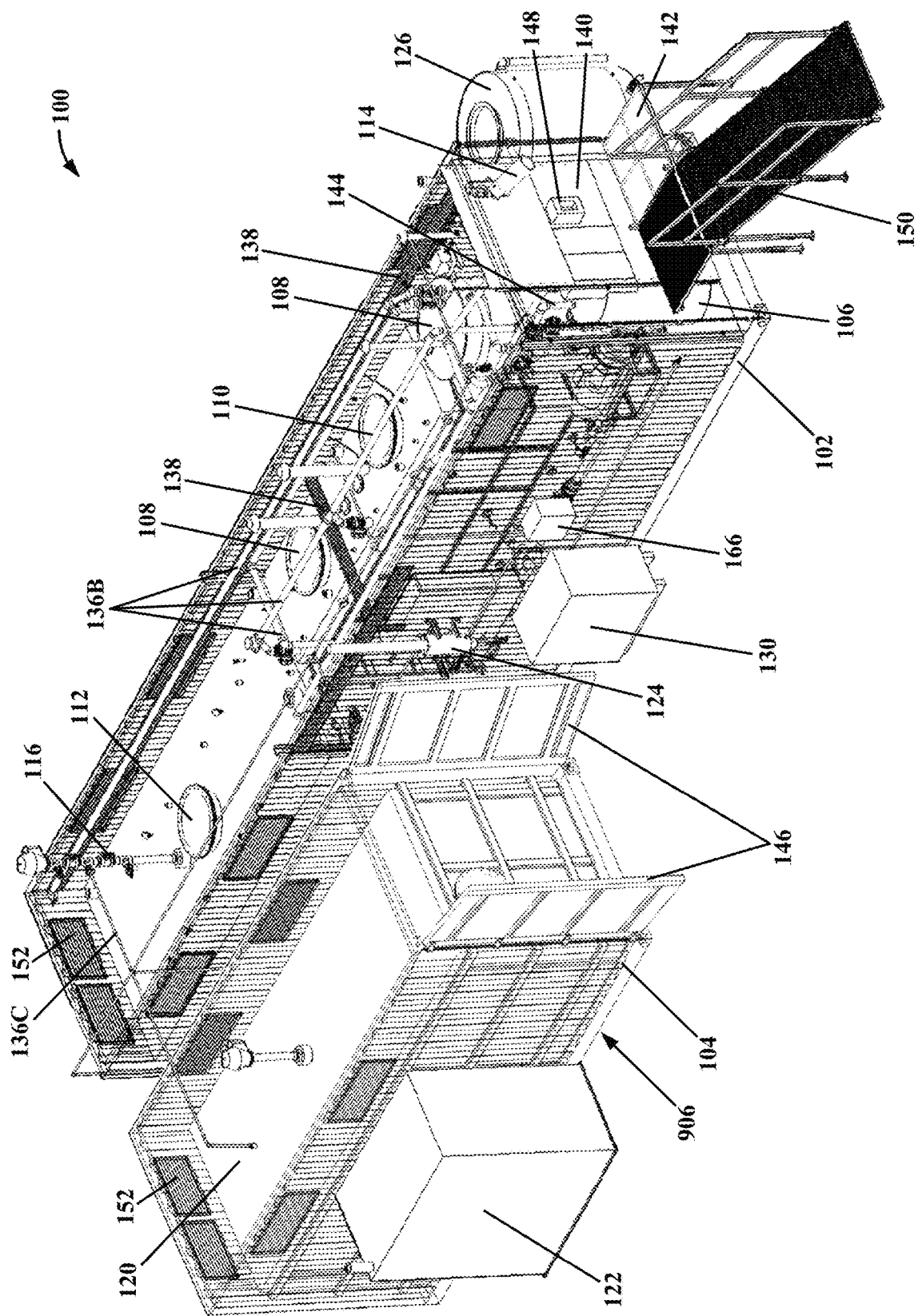
FIG. 1A is an isometric view that illustrates an example of an apparatus for renewable energy microgeneration according to a non-limiting embodiment of the present invention.
Figure 1B:
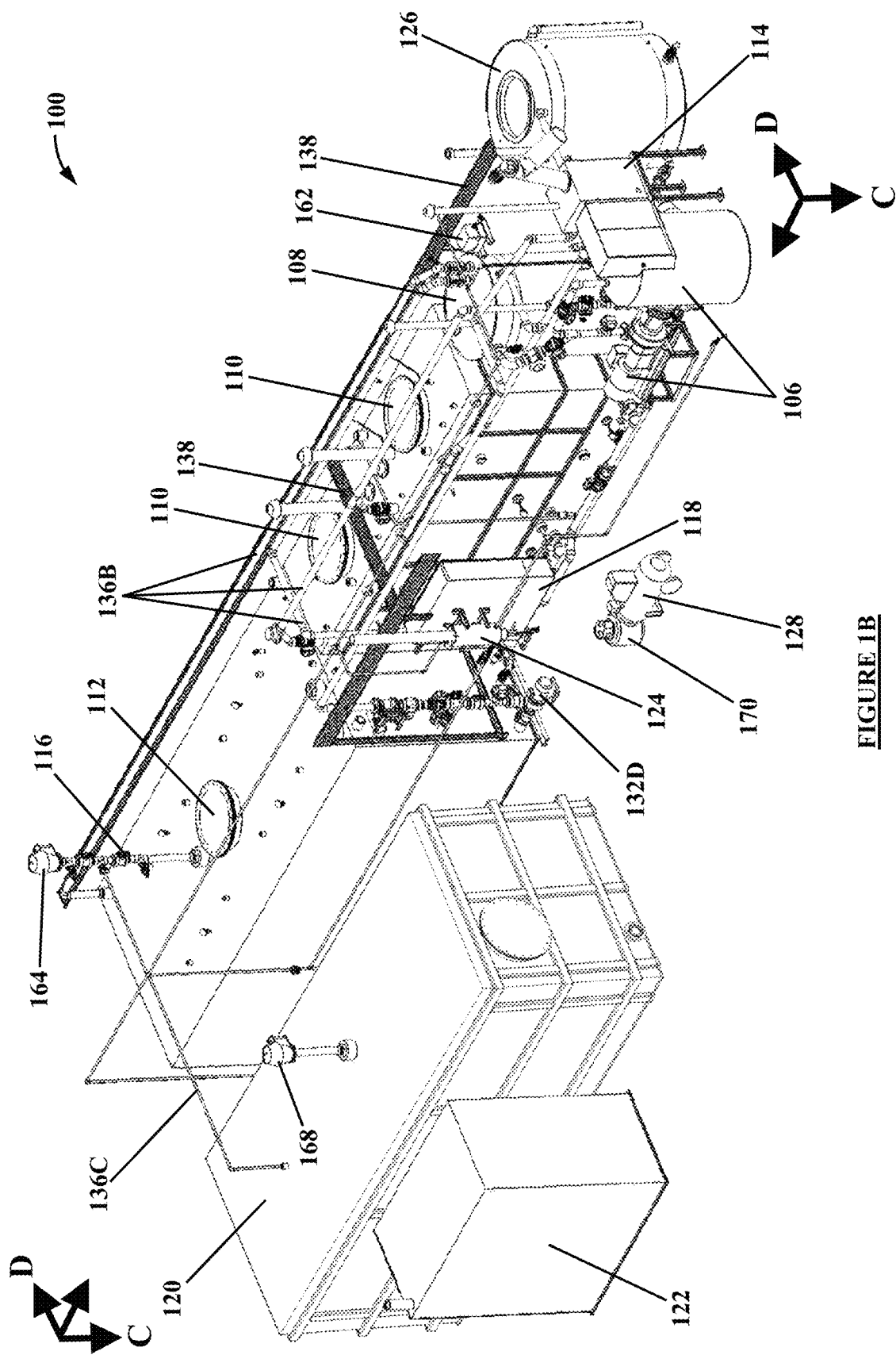
FIG. 1B is an isometric view that illustrates the apparatus of FIG. 1A with the containers and compressor enclosure removed.
Figure 1C:
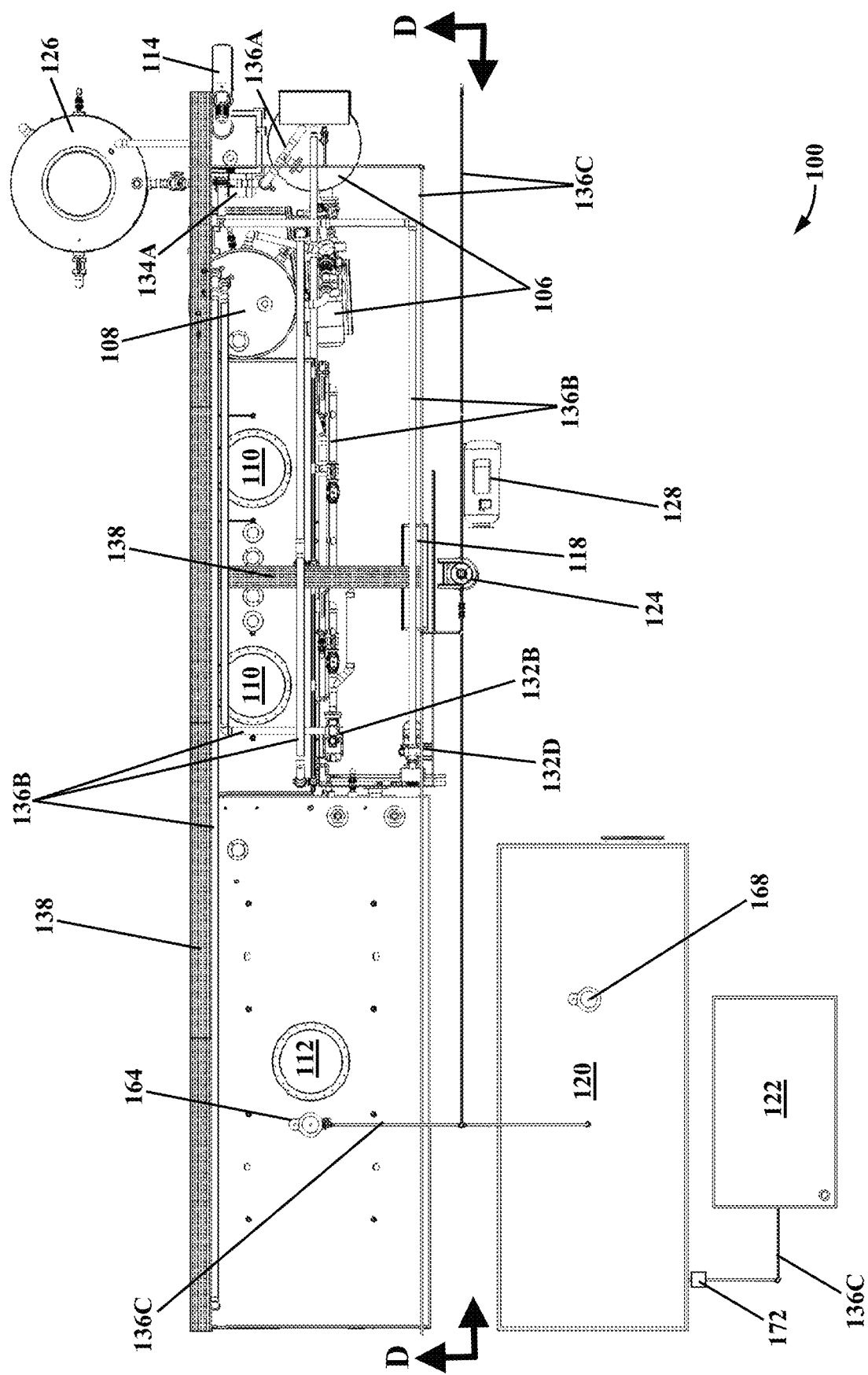
FIG. 1C is a plan view that illustrates the apparatus of FIG. 1B.
Figure 1D:
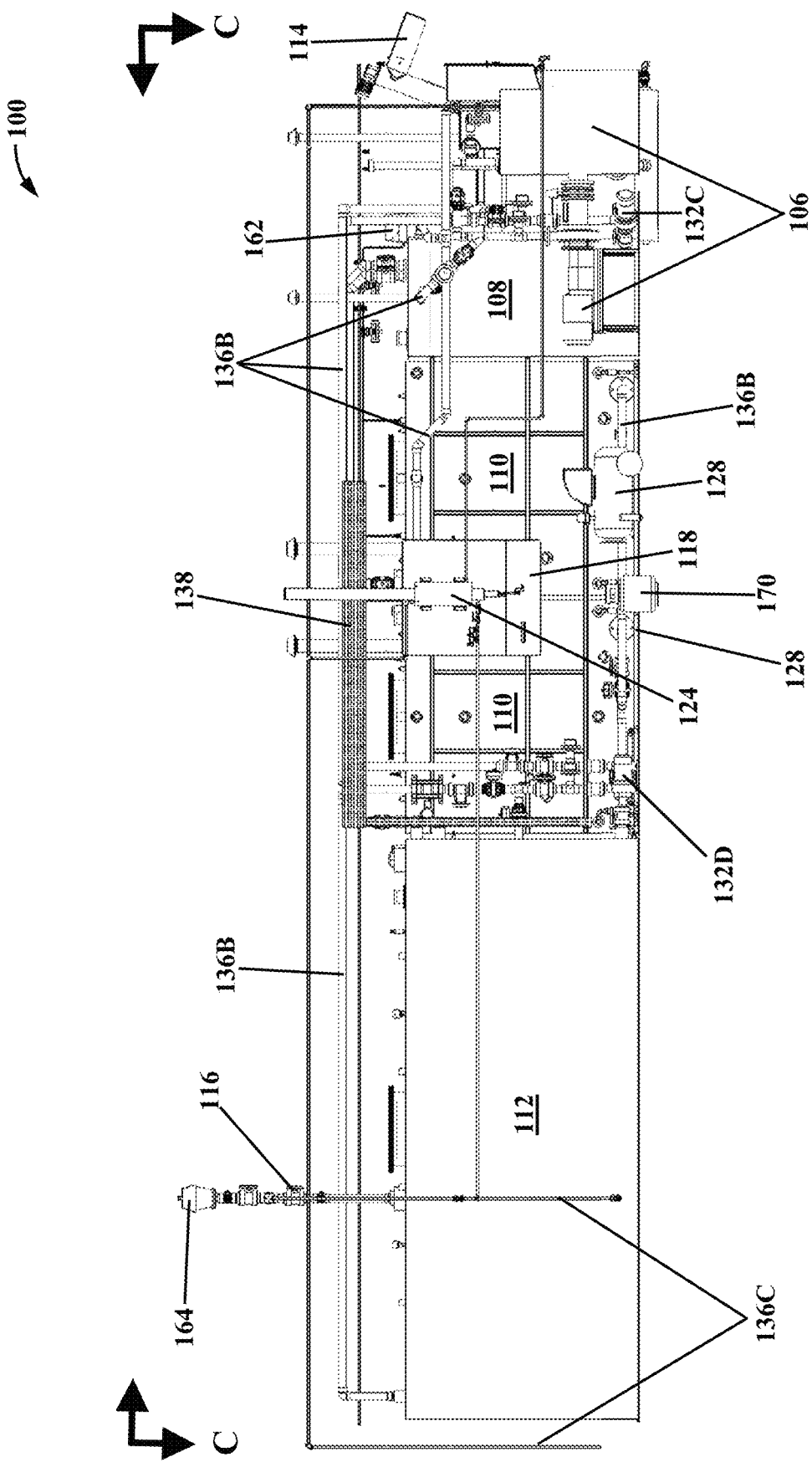
FIG. 1D is an elevation view that illustrates the apparatus of FIG. 1C.

The components in the drawings are not necessarily to scale, emphasis instead being placed upon illustrating the principles of the present invention.

DETAILED DESCRIPTION OF THE INVENTION

The present invention overcomes the shortcomings of the prior art discussed above and offers at least the advantages discussed below by providing a renewable energy microgeneration system in a single, modular, portable configuration that allows users to convert organic waste into sustainable energy onsite. Moreover, it provides a portable renewable energy microgeneration system with a reduced footprint, with modular components and component groupings, and with increased throughput. Accordingly, it can be sized to suit a specific user's needs and can be installed and connected to conventional power systems so that, within a matter of weeks (or hours if the system pre-seeded with live digestate), a user can create his or her own energy for heating, hot water, and/or general electricity needs.

In more detail, the components of the renewable energy microgeneration system work together to perform an anaerobic digestion process that generates heat, electricity, biogas, and fertilizers from what would otherwise be considered "waste." Through its unique configuration, the present invention is able to provide all of the components needed to complete that process in one or more self-contained shipping containers, thereby providing a portable system that can be conveniently connected to a wide variety of structures (e.g., homes, industrial buildings, and outdoor facilities). Moreover, its mobility makes it practical for a wide variety of applications, such as providing power in remote villages, at remote cellular towers, and in war zones or disaster relief areas where waste is plentiful and power and/or heat are in high demand.

In addition to providing power and heat, the renewable energy microgeneration system of the present invention also provides a "green" solution to waste management, maximizing the amount of useful energy that can be harnessed from organic materials. It effectively eliminates the costs of waste removal by providing the user with a close, convenient place to dispose of his or her waste. It also helps eliminate runoff pollution. And, in addition to allowing the user to recycle his or her organic waste onsite, the renewable energy microgeneration system of the present invention also reduces pollution by making the user less dependent on utility companies that generate pollution with their various methods of energy production. Moreover, it reduces carbon emissions from waste transport to a centralized processing facility, such as a dump or a larger-scale anaerobic digestion system.

Those and other advantages provided by the present invention can be better understood from the description of the preferred embodiments below and in the accompanying drawings. In describing the preferred embodiments, specific terminology is resorted to for the sake of clarity. However, the present invention is not intended to be limited to the specific terminology so selected, and it is to be understood that each specific term includes all technical equivalents that operate in a similar manner to accomplish a similar purpose.

A. Apparatus for Renewable Energy Microgeneration

Figure 1E:
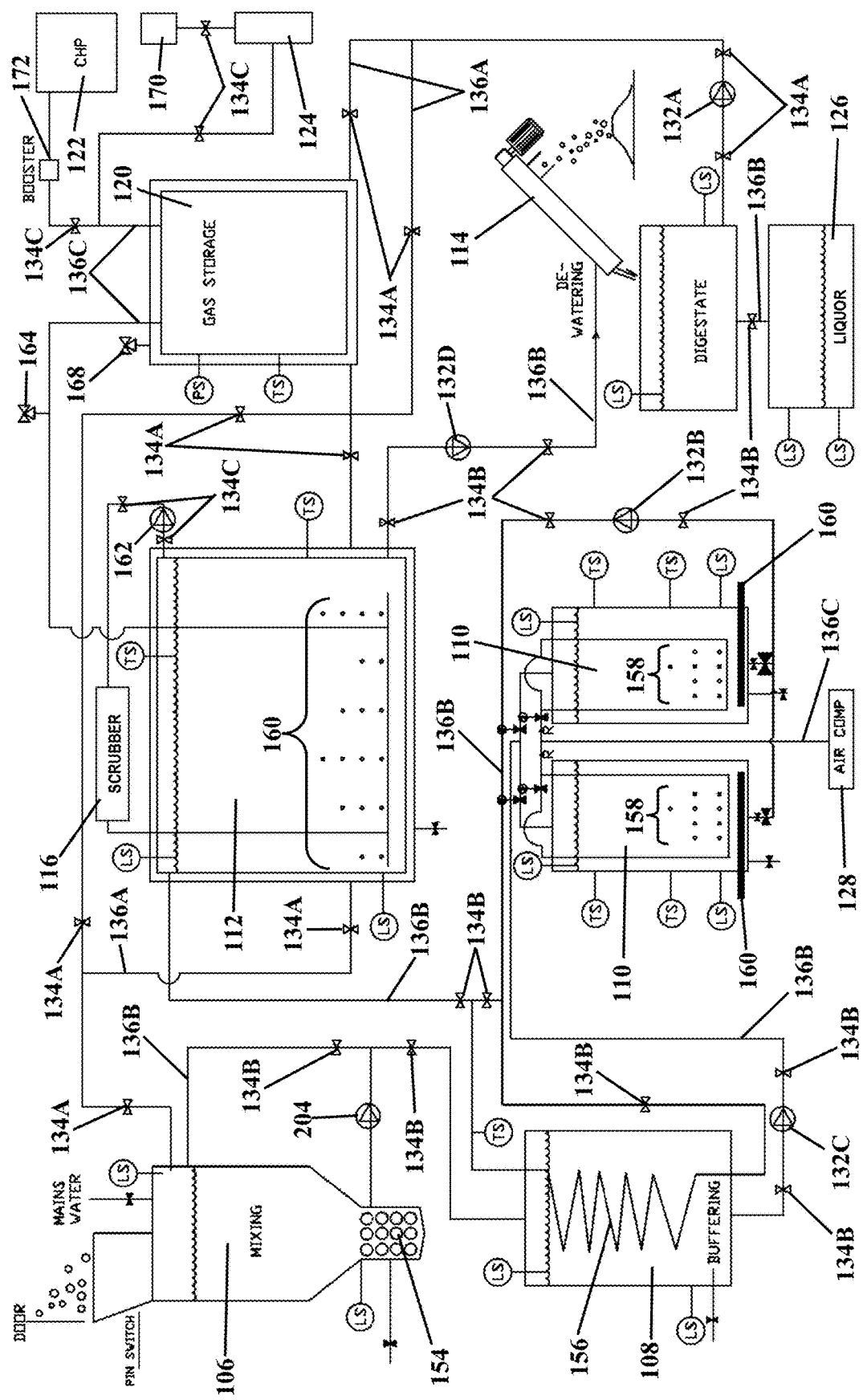
FIG. 1E is a schematic diagram of the apparatus of FIGS. 1A-1CD

Turning to the drawings, FIGS. 1A-1D provide various views of an exemplary apparatus for renewable energy microgeneration 100 (hereinafter "the REM apparatus 100") according to a non-limiting embodiment of the present invention, and FIG. 1E provides a schematic diagram of the REM apparatus 100 according to a non-limiting embodiment of the present invention. That REM apparatus 100 includes a first container 102 and a second container 104 that provide portable enclosures that house the various components 106-128 of the REM apparatus 100. The first container 102 houses a chopper unit 106, a buffer tank 108, two small holding tanks 110, a large holding tank 112, a de-watering unit 114, a gas scrubber 116, and an electronic control unit (ECU) 118. And the second container 104 houses a gas storage unit 906 that includes a gas storage tank 120. The REM apparatus 100 also includes biogas engine 122 disposed adjacent to the second container 104; a flare 124 disposed on the outside of the first container 102; a liquor tank 126 disposed adjacent to the first container 102; a compressor 128 disposed in a compressor enclosure 130 adjacent to the first container 102; and various pumps 132A-132D, valves 134A-134C, piping 136A-136C, and wiring connections 138 for functionally tying those components 106-128 together. The components 106-128 provided in, on, and adjacent to those containers 102 and 104 work together to perform an anaerobic digestion process that generates heat, electricity, biogas, and fertilizers from waste/muck in a mobile, modular renewable energy microgeneration system.

The chopper unit 106 is where muck/waste deposits are loaded into the REM apparatus 100 and it functions to mix that the muck/waste loaded into the REM apparatus 100 and to mix it with liquid (e.g., potable and/or grey water). The buffer tank 108 functions to store and pre-warm the water/muck/waste mixture produced with the chopper unit 106. The small holding tanks 110 function to pasteurize the pre-heated water/muck/waste mixture produced with the buffer tank 108 or, when pasteurization is not required for the overall anaerobic digestion process, to partially digest that pre-heated water/muck/waste mixture via thermophilic anaerobic digestion. The large holding tank 112 functions to produce mesophilic anaerobic digestion with the partially pasteurized or digested water/muck/waste mixture produced with small holding tanks 110. The de-watering unit 114 functions to remove liquids from what remains of the water/muck/waste after anaerobic digestion is completed in the small holding tanks 110 and/or the large holding tank 112. The gas scrubber 116 functions to clean the biogas produced during thermophilic and/or mesophilic anaerobic digestion in the small holding tanks 110 and/or the large holding tank 112, respectively. The gas storage tank 120 functions to store the cleaned biogas produced with the gas scrubber 116. The biogas engine 122 functions to simultaneously generate electricity and heat from the cleaned biogas stored in the gas storage tank 120. The ECU 118 functions to control the flow of liquid, muck/waste, water/muck/waste, and biogas through the REM apparatus 100 as required to generate heat, electricity, biogas, and fertilizers in a continuous, regenerative cycle. The flare 124 functions to safely burn surplus biogas. And the compressor 128 functions to generate compressed air for stirring the water/muck/waste mixture in the small holding tanks 110. The containers 102 and 104 and each of those components 106-128 are addressed separately below.

i. Containers 102 and 104

To enable the REM apparatus 100 to be transported as modular units to substantially any location, the containers 102 and 104 that house the various components 106-128 of the REM apparatus 100 are configured to comply with the size and weight requirements of the relevant highway regulatory and governmental agencies. In FIG. 1A, for example, the first container 102 (shown with top removed) is a standard 40-foot "High Cube" shipping container (40 ft×8 ft×9.5 ft; Payload: 60,350 lbs; Capacity: 2,376 ft$^3$) and the second container 104 (also shown with top removed) is a standard 20-foot shipping container (Dimensions: 19.8 ft×8 ft×8.5 ft; Payload: 48,600 lbs; Capacity: 1,164 ft$^3$). Such containers are specifically designed to be handled by ship-to-shore gantry cranes, to be stacked and stored on a container ship, and to be attached to a container transport trailer, thereby making those containers 102 and 104 particularly suited for commercial land and sea transport. Those containers 102 and 104 are also particularly suited for military air transport using certain military aircraft, such as Sikorsky SKYCRANE brand helicopter and the Lockheed C-130 HERCULES brand airplane. Other standard containers may also be used (e.g., 45-foot and 30-foot containers).

As an alternative to the configuration depicted in FIGS. 1A-1D, the various components 106-128 of the REM apparatus 100 also may be housed in a plurality of smaller containers (e.g., a combination of 10-foot and 20-foot shipping containers rather than a 40-foot shipping container 102 in combination with a 20-foot shipping container 104). As depicted in FIGS. 9-19, for example, the chopper unit 106 may be housed in a 10-foot container 1000, while a command unit 902, a digester unit 904, the gas storage unit 906, and the dewatering unit 114 may be housed in separate 20-foot containers 104, 1100, 1200, and 1300. The REM apparatus 900 may include one of each of these units 106, 114, 902, 904, and 906, or it may include a plurality of one of more of each of these units 106, 114, 902, 904, and 906, as required to expand capacity according to the needs of the user. For example, one chopper unit 106, one command unit 902, one gas storage unit 906, and one dewatering unit 114 may be configured to be used with between one and five digester units 904 such that increased CHP production is achieved with the addition of each digester unit 904, but without the need to increase the footprint of the REM apparatus 900 and without the need for additional chopper units 106, command units 902, the gas storage unit 906, or dewatering units 114. The separation of these units 106, 114, 902, 904, and 906 in this manner allows for more unique stacking configurations, particularly in a city environment where 40-foot shipping containers may not be a feasible option. Additionally, the separation of these units 106, 114, 902, 904, and 906 allows for spatial separation of the various units 106, 114, 902, 904, and 906, particularly the digester unit 904 and the gas storage unit 906, for safety and other considerations.

In addition, the containers of the REM apparatus 100 and 900 may include all piping 136A-136C and 1006 internally for safety during operation. Additionally, the internal piping configuration allows for the safe transport of the various containers by minimizing the chance for damage to external components of the standardized containers.

Figure 10A:
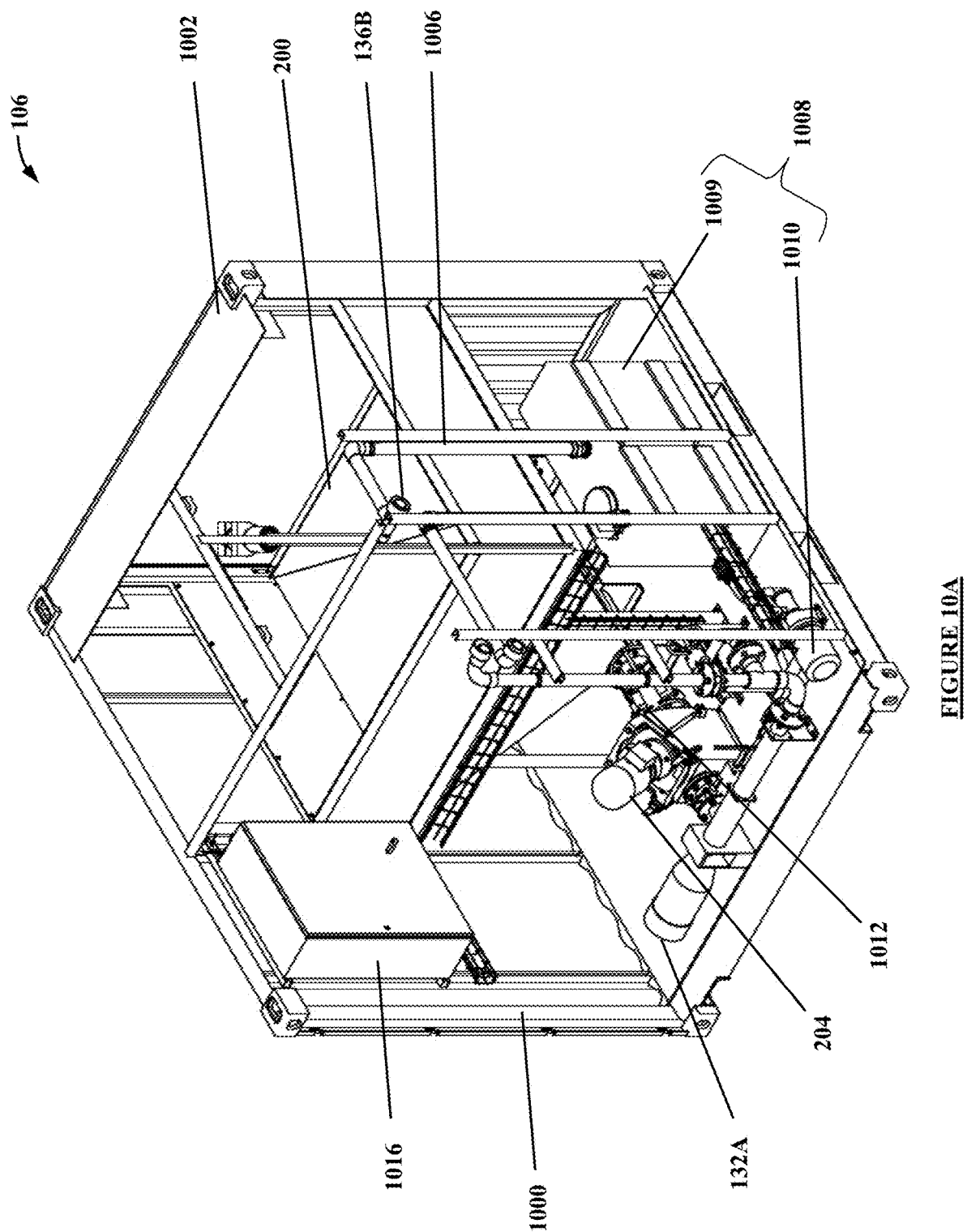
FIG. 10A is an isometric view that illustrates a chopper unit according to the non-limiting embodiment of the present invention depicted in FIGS. 9A and 9B.
Figure 10B:
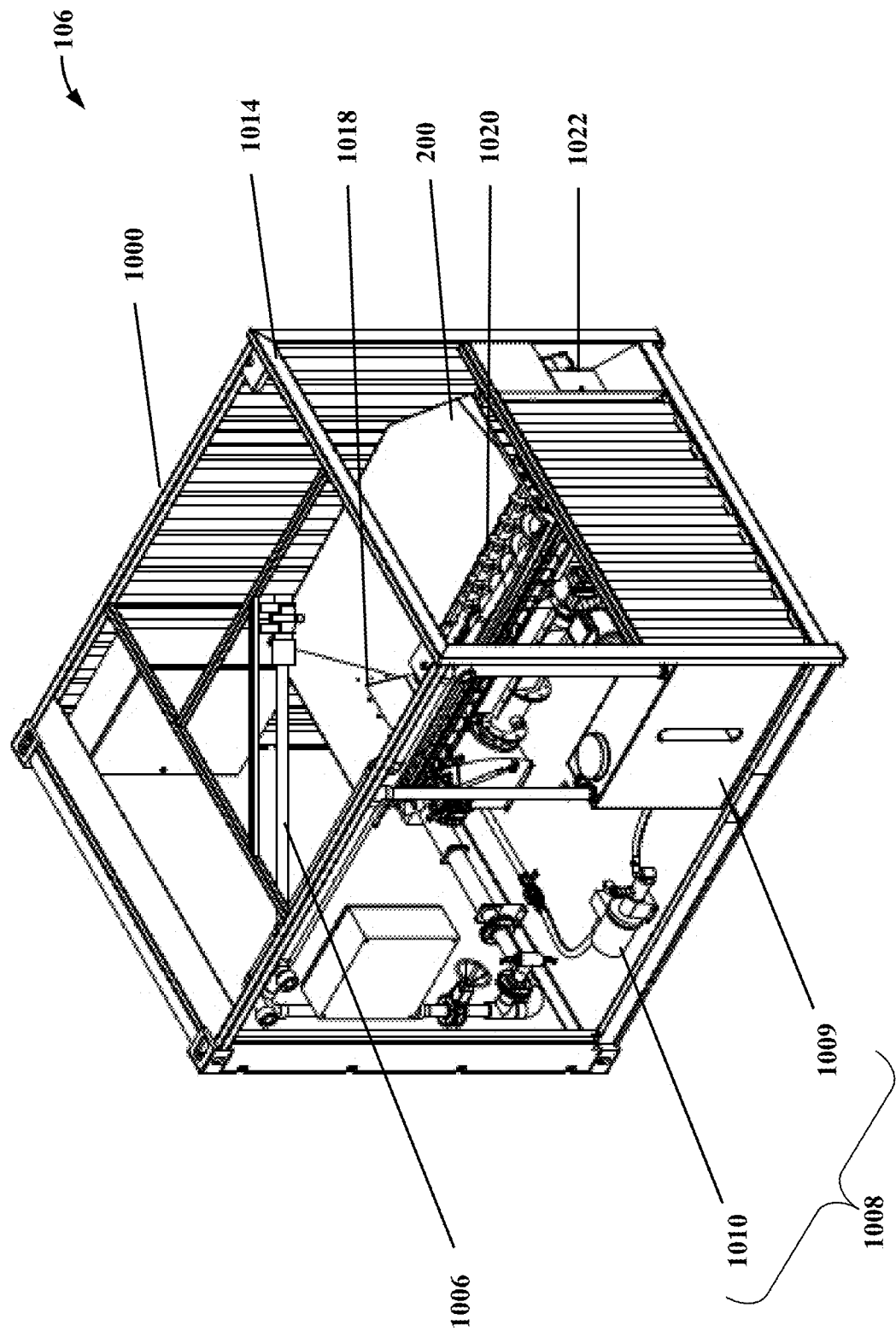
FIG. 10B is an isometric view that illustrates another chopper unit according to a non-limiting embodiment of the present invention depicted in FIGS. 9A and 9B.

The REM apparatus 900 may comprise a chopper unit 106, stored in a 10-foot container, that houses, a shutter door 1014, bin lifter (not depicted), a hopper 200, a hopper scraper 1018, a feed auger 1020, a homogenizing pump 204, a feed pump 132A, a liquor dosing system 1008, and an odor abatement pipeline 1006, as depicted in FIG. 10B. As above, the chopper unit 106 is where muck/waste deposits are loaded into the REM apparatus 900 and it functions to mix that the muck/waste loaded into the REM apparatus 900 and to mix it with liquid (e.g., potable and/or grey water). The separation of the chopper unit 106 from the container 102 allows for multiple chopper units 106, a variety of chopper unit styles, or the complete removal of the chopper unit 106. The command unit 902, stored in a 20-foot container, may comprise the ECU 118, the buffer tank 108, the liquor tank 126, the small holding tanks 110, a central drainage line 1007, and an odor abatement pipeline 1006. The command unit 902 provides similar functionality as each of the component parts of the system described previously. The separation of the command unit 902 from container 102 gives the REM apparatus 900 the flexibility to use a single command unit 902 with multiple chopper units 106 or multiple digester units 904. Digestate from the command unit 902 travels to the digester unit 904, stored in a 20-foot container, which may comprise the large holding tank 112, a large holding tank heating system 1206, a large holder tank recirculation system 1208, a large holder tank discharge pump 1204, a large holder tank pressure relief valve 164, methane sensor 1202, and a large holder tank drainage connection 1210. Storing the large holding tank in a separate container allows for users to significantly scale up the power generated from the REM apparatus 900 by simply adding more digester units 904 and/or gas storage unit 906. The biogas generated by the digester unit 904 is scrubbed by the gas scrubber 116 and stored in the gas storage tank 120. The gas storage tank 120, contained in a 20-foot container, may comprise a flexible bladder 500, a gas holder discharge system, and a gas level switch assembly. The odor abatement unit 908 may comprise the central odor abatement pipeline 1006, which is used to transfer odorous atmosphere from the components of the REM apparatus 900 to the odor abatement unit 908. The heating system comprises the central heating pipeline and the boiler system 922. The combined heat and power unit (CHP) may comprise the gas scrubber 116, the prime mover, the generator 918, and the heat recovery system. The grid connection interface cabinet 920 comprises at least a protection device (not depicted), an import/export meter (not depicted), and a gas leak detection device (not depicted).

a. Base

The first container 102 includes a concrete base that houses some of the piping 136A-136C that interconnects the components 106-128 of the REM apparatus 100. In manufacture, that piping 136B and 136C is assembled using a jig to ensure that all the components 106-114 can be positioned correctly in a repeatable, modular manner. The jig is manufactured using an inverse profile of those components 106-114. A straw-based concrete is preferably used to form the base of the container 102 because it is a sustainable material that provides a certain degree of flexibility within the concrete base.

The concrete base is designed to support the various components 106-114 in the first container 102 by following the profile of the tank bases. That configuration not only provides stability along with the exterior walls that hold the tanks in place, it also braces those components 106-114 so as to ensure the pipe fittings will not shear in transport. Those components 106-114 may be further braced within the container 102 with insulation designed to fit tightly between those specific components 106-114 and the container 102. In the alternative, the base of the first container 102 may include a metal framework to create strength and allow for glide entry of the components 106-114 into the first container 102.

b. Facia 140 and Loading Platform 142

The first container 102 also includes facia 140 and a loading platform 142 at one end of for use in loading muck/waste into the chopper unit 106 and for unloading fertilizer output by the de-watering unit 114. The facia 140 includes a door 144 that can be opened to allow users access to the various components 106-114 housed therein. The first container 102 also includes a pair of external double doors 146 at the same end of the first container 102 as the facia 140. Although those doors 144 are not shown on the first container 102 for purposes of clarity, they are clearly shown on the second container 104. Those doors 146 are of the type typically found on a conventional 40-foot or 20-foot shipping container.

The facia 140 provides protection to the user from the components 106-114 housed in the first container 102. And the door 144 provides access for maintenance and safety checks to be performed on those components 106-114. The facia 140 may also include access panels (not shown) for accessing parts on the far sides of the components 106 and 114 that are disposed adjacent to the facia 140 so as to provide the maximum amount of access and maneuverability to users that need to perform maintenance and/or safety checks on those components 106 and 114.

The loading platform 142 is configured allow muck/waste to be loaded into the chopper unit 106 and to allow solid waste (e.g., mulch) to be transported away from the de-watering unit 114 using a wheelbarrow or other comparable wheeled transport device. The loading platform 142 is also configured to fold up between the facia 140 and the pair of double doors 146 so it can be stowed away during transport of the first container 102. A control box 148 for operating and monitoring the REM apparatus 100 via the functionality of the ECU 118 is also provided on the facia 140 and will be folded up behind the double doors 146 of the second container 102 during transport. Emergency stop and full shut offs are also located on the facia 140. Because there should not be a need to access the gas storage tank 120 after the REM apparatus is placed into operation (other than routine maintenance and safety checks) that component 120 preferably remains secured behind the double doors 146 of the second container 104 during transport and during operation of the REM apparatus 100.

The loading platform 142 is strong enough to support significantly more weight than that of the user so large amounts of muck/waste can be loaded into the anaerobic digester at one time. A ramp 150 is also be provided with the loading platform 142 to allow wheeled transport devices, such as wheelbarrows, to be easily moved to and from the top of the loading platform 142. The ramp 150 is constructed from standard square tubes, welded together with mesh spot welds on the top, which provides a tractable surface for all weather conditions. The ramp 150 is removably attached to the loading platform 142 using angled hooks that clip into a corresponding receiver on the loading platform 142, which allows users, such as horse yards, to remove the ramp 150 and use their existing ramps in its place. The loading platform 142 and ramp 150 are preferably made from galvanized steel to protect them from the elements and to reduce manufacturing costs. And the legs of the platform 142 and ramp 150 are preferably adjustable according to different terrain to provide maximum stability, such as on uneven surfaces.

In the REM system 900 that comprises a plurality of smaller containers 106-128 and 902-908, the chopper unit 106, which is where muck/waste are loaded into the system, may comprise a catering mouth 1002, instead of a facia 140, as depicted in FIG. 10A. The catering mouth 1002 includes a roller shutter door (not depicted) that extends the width of the chopper unit 106 to allow larger quantities of muck/waste to be processed by the chopper. The roller shutter door of the catering mouth 1002 opens and closes vertically, although other embodiments may incorporate other door mechanisms based on the application. The catering mouth 1002 allows access to load feedstock into the hopper inside the container at a reasonable height without the need for a loading platform. A safety interlock system prevents all chopper operations while the catering mouth 1002 is open.

In another embodiment, the REM system 900 may include a separate septic input option (not depicted) which may be used in conjunction with, or instead of, the facia 140 or the catering mouth 1002. This septic input option would funnel septic or sludge waste directly into either the chopper unit 106 or into the buffer tank 108. This septic input provides another mechanism for users to drive the anaerobic digestion of the REM apparatus 100 or 900 based on the type of muck/waste generated by the user. This septic input option may also provide a pipeline for alternative types of grey water/muck/waste to be inputted into the system. The chopper unit 106 may be configured to fit behind the doors of a standard container to allow for shipping of the chopper unit 106. The contents 108-128 of the other containers 902-908 also should be configured to fit behind the doors of a standard container to allow for shipping.

c. Ventilation

A forced ventilation system is preferably incorporated into each container 102 and 104 to prevent build-up of an odorous and explosive atmosphere. That forced ventilation system includes an electric fan (not shown) that generates a pressure differential between the inside of each container 102 and 104 and the atmosphere so as to circulate air through each container 102 and 104 via louvers 152 provided therein. That process not only prevents dangerous gases from building up in the containers 102 and 104, it also removes heat to help cool the machinery located in the first container 102. A roof circular vent (not shown) may also be provided to allow heat to escape while preventing the ingress of water. If the electric fan fails, the ECU 118 will produce an alarm and initiate shutdown of the various components 106-128 of the REM apparatus 100.

The ventilation system may also include an air sparge system (not depicted) designed to ensure a certain level of oxygen to be present inside the various containers in the REM apparatus 100 and 900 to prohibit the production of biogas inside the various containers through the process of anaerobic digestion. The air sparge system consists of a linear air pump (not depicted) that pumps air into an air line. The air line is fed into the necessary tanks near the base of the tank, where it forms a perforated loop that allows an even release of air. The linear air pump is electrically driven. It is sized to deliver sufficient air to inhibit the production of biogas and, in case any gas is produced, to sufficiently dilute these gases to prevent a flammable or explosive condition inside the tank. The air sparge system is manufactured from materials that provide resistance to corrosion and erosion for 20 years.

Additionally, the forced ventilation system and the roof circular vent may be attached to an odor abatement pipeline 1006 (FIG. 10) to transfer the odorous or explosive atmosphere to be processed. In this embodiment, only the excess atmosphere that is unable to be sent to the through the odor abatement pipeline 1006 to the odor abatement system 908 (FIG. 11) will be vented.

d. Roof

The first container 102 and second container 104 may include radiator roofs that use flexible water piping 136A to heat water using the sun's energy. Because such standard containers have grooves formed in their roofs, the flexible water piping 136A can be laid out in those grooves. That water piping 136A will be is covered with a UV-protected plastic sheet to encapsulate heat and, in turn, heat the water within that piping 136A. Solar panels may also be placed on the roofs of the first container 102 and the second container to heat water and/or generate electricity using the sun's energy. That warm water and electricity can be used to support the operation of the other components 106-128 of the REM apparatus 100 (e.g., heating muck/waste and/or powering pumps 132A-132D and other electronics) and/or it can be used to supplement the heat and electricity generated with the biogas engine 122. Rain water may also be harvested from the roofs of the containers 102 and 104 for use in the chopper unit 106. The roofs may also include a lightning rod, or equivalent device, for protecting the containers 102 and 104 and their contents from lightning strikes.

Additionally, solar thermal/electric panels may be incorporated or attached to the roofs of the containers 102, 104, 1000, 1100, 1200, and 1300 in order to supplant the CHP used by the REM apparatus 100 and 900. These solar panels may be controlled by the ECU 118.

ii. Chopper Unit 106

The chopper unit 106 may be disposed at a distal end of the first container 102. Alternatively, the chopper unit 106 may be housed in a separate, 10-foot container 1000, as depicted in FIGS. 9-10. The chopper unit 106 functions as the input facility for loading muck/waste deposits into the REM apparatus 100 or 900. The chopper unit 106 also may include an air compressor (not depicted) for use in automatically opening and closing valves 134 therein.

Figure 2:
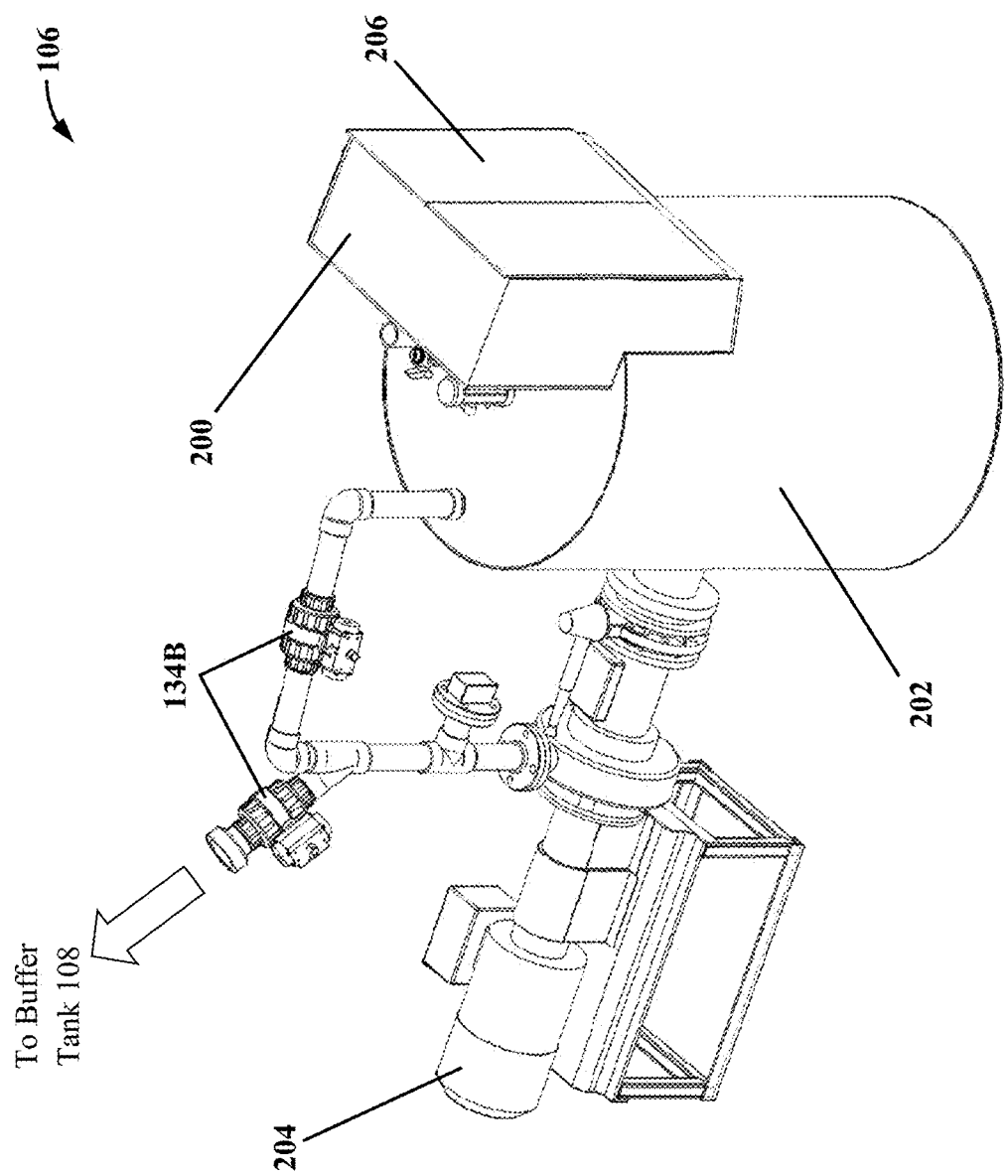
FIG. 2 is an isometric view that illustrates a chopper unit according to a non-limiting embodiment of the present invention.

As FIG. 2 illustrates, the chopper unit 106 may include a hopper 200, a mixing tank 202, and a homogenizing pump 204. The hopper 200 is formed as the opening of the chopper unit 106 to facilitate easier loading of muck/waste therein. The hopper 200 includes a pair of doors 206 that must be opened to load the chopper unit 106. Those doors 206 are accessible at the facia 140 of the first container 102 and are held closed with magnetic catches. The hopper 200 is preferably made from stainless steel or other corrosion resistant material (e.g., galvanized steel) because it is likely to be hit and scratched by shovels/spades or other loading equipment, and the doors 206 are preferably made of a durable transparent material (e.g., plexiglass) so a user can view the mixing/macerating process when the doors 206 are closed. Those doors 206 also provide a safety feature by preventing operation of the chopper unit 106 when they are opened, thereby preventing a user or a tool from being pulled into the mixing tank 202 by the homogenizing pump 204. That functionality is controlled by the ECU 118.

As depicted in FIG. 10A and noted above, the chopper unit 106 may comprise a catering mouth 1002 with automated roller shutter doors instead of a pair of hinged doors 206. The catering mouth 1002 allows access to load feedstock into the hopper 200 inside the container at a reasonable height. A safety interlock system prevents all chopper operations while the shutter door is open. The chopper unit 106 may also include a septic input option (not depicted) which feeds directly into the mixing tank 202. The catering mouth 1002 may be housed within a 10-foot shipping container, with container blocks on each corner of the container, to enable the handling and stacking advantages of shipping containers. Multiple chopper units 106 can be integrated into the REM apparatus as needed. The container is modified to provide an opening for the roller shutter door and to allow pipework for input and output to penetrate the container sides. All openings and penetrations are reinforced to maintain structural integrity. The cargo doors are retained to provide access for maintenance. With the cargo doors of the container 1000 and the roller shutter door of the catering mouth 1002 closed (e.g. when not in maintenance), the container is fully enclosed on all sides to prevent rodents, birds and other animals from entering. A safety interlock prevents all operation while the container doors are open.

The roller shutter door of the catering mouth 1002 allows access to load feedstock into the receiving hopper 200 inside the container 1000. The door is controlled via the control unit 1022 on the outside of the chopper unit 106. A safety interlock prevents all chopper operation while the shutter door 1002 is open. The chopper unit 106 can be loaded with feedstock manually or can be equipped with a bin-lifter (not depicted) to assist the loading process. The loading mechanism may vary per case and is selected based on the waste collection characteristics (waste container type and size, frequency, etc.) of a specific case. In this embodiment, the loading point of the chopper unit 106 is referred to as a catering mouth 1002 because it is particularly suitable for receiving and processing food waste.

The chopper unit 106 also functions to homogenize the muck/waste that is moved into the mixing tank 202 via the hopper 200. Liquid (e.g., potable and/or grey water) is fed into the chopper unit 106 via water piping 136A and mixed with the muck/waste in the mixing tank 202 using the homogenizing pump 204 to re-circulate, macerate, and homogenize the liquid and muck/waste. Alternatively, the liquid fed via the water piping 136A may be use grey water stored in the liquor dosing tank 1009 to remove the need for external potable water. The water/muck/waste mixture is chopped finely enough by the homogenizing pump 204 that it will not clog the waste valves 134B or the waste piping 136B of the REM apparatus 100 as it moves between the components 106-114 thereof. Liquid is pumped into the mixing tank 202 by a mixer feed pump 132A as required to provide the proper mixture of liquid and muck/waste in the mixing tank 132 required for hydrolysis. That flow rate is controlled by the ECU 118 based on the amount of muck/waste deposited in the mixing tank 202. And the liquid is preferably grey water that is re-circulated from the de-watering unit 114 back into the mixing tank 202 in a regenerative manner to further add to the efficiency of the REM apparatus 100.

The mixing tank 202 is positioned below with hopper 200 so muck/waste is fed directly into the mixing tank 202 via the hopper 200. The mixing tank 132 preferably includes an integrated stone trap 154 (FIG. 1E) to catch larger debris that that might clog the waste valves 136B or the waste piping 128B. The stone trap 154 will need to be discharged on regular basis determined after commissioning of the REM apparatus 100 and is therefore preferably accessibly via an access hatch in the facia 140. The chopper unit 106 can be sized to meet the output requirements of the user and/or the particular type(s) of muck/waste being processed. And because muck/waste types generally have high volume and low weight or high weight and low volume, the mixing tank 202 will have a visible level marker to which the mixing tank 202 can be filled with substantially any type of muck/waste without exceeding the limits of the REM apparatus 100.

The volume indicated by that level marker (e.g., 60 Liters) includes both the muck/waste loaded into the mixing tank 202 by the user and the liquid fed into the chopper unit 106 via the water piping 136A. The ECU 118 will automatically determine the appropriate amount of liquid to mix with the waste/muck based on the weight and type of the waste/muck. For example, very dry and/or dense waste/muck (e.g., horse manure) may require a dilution ratio up to 9:1, while wetter and/or less dense waste/muck (e.g., vegetable waste) may require a dilution ration of around 4:1. Because the dense waste/muck necessarily weighs less than the less dense waste muck, the resulting overall volume of water/waste/muck in the mixing tank 108 will be the same regardless of which of those types of waste/muck is placed therein (i.e., 15 kg horse manure and 45 kg of vegetable waste will both fill a 60 Liter volume when the proper amount of liquid is added). The type and/or weight of the waste/muck can be input into the ECU 118 by a user and/or automatically measured by the ECU 118, such as with an electronic scale, so the ECU 118 can determine the appropriate amount of liquid to mix with that waste/muck.

In the REM apparatus 900 depicted in FIG. 9, the chopper unit 106 may comprise the hopper 200, the homogenizing pump 204, the feed pump 132A, a liquor dosing system 1008, and an odor abatement pipeline 1006. The hopper 200 can be reached by opening the roller shutter door of the catering mouth 1002, which allows access through a rectangular opening large enough to receive loading from containers sized up to 360-liter bins. The hopper assembly 200 comprises the receiving hopper 200, hopper scraper 1018, and a feed auger 1020, and auger motor 1012.

The loaded feedstock is received by a 2,000-liter receiving hopper 200 that may allow 3,000 kg of fresh feedstock per day to be loaded in at least four feeding sessions. The sides of the hopper 200 are sufficiently sloped to allow gravity to force the feedstock down to the bottom of the hopper 200, where it enters a trough that houses the feed auger 1020. The hopper 200 and the auger trough may be manufactured from mild steel with an appropriate coating to provide resistance to corrosion and erosion for 20 years.

The hopper scraper 1018 is a pneumatically operated device that is mounted on one of the sloped sides of the receiving hopper 200. It is designed to assist the feedstock in the hopper 200 to enter the auger 1020 and to prevent 'bridging' of feedstock in the hopper 200.

The feed auger 1020 is an electrically driven screw conveyer mounted in the trough at the base of the hopper 200. It receives the feedstock from the hopper 200 and conveys it to the homogenizing pump 204. The auger 1020 has an appropriate capacity that meets the through-put requirements of at least 3,000 kg of feedstock per day.

The feed auger 1020 conveys the food waste from the receiving hopper 200 into the homogenizing pump 204. The homogenizing pump 204 reduces the particle size of the feedstock to a maximum of 5 mm. The specific homogenizing pump 204 is selected based on appropriate throughput capacity that allows at least 3,000 kg of feedstock per day to be processed. It has a facility that collects and allows easy removal of large, solid objects that cannot be processed, such as cutlery, crockery and glass. Inside the homogenizing pump 204, the freshly macerated feedstock is mixed and diluted with liquor from the liquor dosing system 1008.

a. Liquor Dosing System 1008

As depicted in FIGS. 10A and 10C, the liquor dosing system 1008 includes a dosing tank 1009 and a dosing pump 1010. The dosing tank 1009 is a small polymer tank disposed inside the container 1000 that houses the chopper unit 106. It is filled with liquor from the liquor tank 126, and its content is used to mix with and dilute fresh, macerated feedstock to reduce the level of suspended solids in the feedstock flow. A level indicator inside the dosing tank 1009 allows the ECU 118 to interrupt all chopper operation when the dosing tank 1009 level is running low, allowing liquor flow from the liquor tank 126 into the dosing tank 1009 when the dosing tank level is running low, and prevent liquor flow from the liquor tank 126 into the dosing tank 1009 when the dosing tank level is high. The dosing pump 1010 is an electrically driven compact progressive cavity pump that pumps the liquor from the dosing tank 1009 into the homogenizing pump 204.

The liquor dosing system 1008 is operated as needed based on feedstock fluidity and is designed to reduce the level of suspended solids of the fresh feedstock to match the limitations of a dosing pump 1010 for a particular waste stream or a particular market. The level of suspended solids may range from 6% to 72% ("feedstock dilution"). The liquor dosing system 1008 automatically pumps part of the produced liquor from the liquor tank 126 in the command unit 902 or container 102 to the chopper unit 106. In the chopper unit 106, the liquor is mixed with the freshly chopped feedstock to ensure the feedstock mix is sufficiently fluid to be pumped through the system. Using liquor instead of fresh water for this process eliminates the requirement of additional clean water input and maximizes the amount of energy that is extracted from the feedstock during the digestion process. This process is controlled by the ECU 118 based on the feedstock processed. Dilution takes place in the homogenizing pump 204, before the feed pump 132A, allowing the diluted mix to be pumped into the buffer tank 108 by the feed pump 132A.

The liquor dosing system 1008 also may include additional tanks (not depicted) with segregation columns and sampling points. The segregation columns and sampling points include sensors for monitoring feedstock fluidity so the ECU 118 may better control the dosing process. The segregation columns and sampling points also may be configured to allow access by users of the REM apparatus 900 for manual and/or visual fluidity assessment.

b. Odor Abatement Pipeline 1006

The odor abatement pipeline 1006 in the chopper unit 106 is designed to abate the odor from at least the liquor dosing tank 1009, the buffer tank 108, the small holding tanks 110, the large holding tank 112, and the open air space above the receiving hopper assembly 200. The air contained in the open air space above the receiving hopper assembly 200 is actively attracted into the odor abatement pipeline 1006 by a fan. Alternatively, the connection to the tanks may be passive such that the air inside the tank is displaced through the pipeline during filling and emptying of the tank. The odor abatement pipeline 1006 leaves the chopper unit 106 through the wall of the container and is led into the system's external odor abatement system 908. The odor abatement system 908 can optionally be installed in the command unit 902.

iii. Command Unit 902

The command unit 902 may be in housed in the container with various components 106-128, or may be stored separately in a 20-foot container. The command unit 902 may comprise the ECU 118, the buffer tank 108, the liquor tank 126, the small holding tanks 110, a central drainage line 1007, and an odor abatement pipeline 1006. The command unit 902 provides similar functionality as each of the component parts of the system described separately. However, the separation of the command unit 902 from container 102 gives the REM apparatus 900 the flexibility to use a single command unit 902 with multiple chopper units 106 or multiple digester units 904. Digestate processed from the command unit 902 travels to the digester unit 904.

a. Buffer Tank 108

The buffer tank 108 receives the water/muck/waste mixture from the chopper unit 106 and stores it before moving it to the small holding tanks 110. Because it is used for storage rather than just mixing, the buffer tank 108 is sized larger than the mixing tank 202 of the chopper unit 106. The water/muck/waste mixture is moved from the mixing tank 202 of the chopper unit 106 to the buffer tank 108 with the homogenizing pump 204 by opening one waste valve 134B and closing another so as to close the re-circulation loop and re-direct the water/muck/waste mixture to the buffer tank 108. The opening and closing of those waste valves 134B is controlled by the ECU 118 based on predetermined cycle times.

The buffer tank 108 functions as a "buffer" for the small holding tanks 110 and large holding tank 112 by warming the water/muck/waste mixture before it is moved into the small holding tanks 110 and large holding tank 112. That warming is preferably performed by a heat exchanger 156 that is disposed in the buffer tank 108. The heat exchanger 156 receives heat energy by pumping the heated and partially pasteurized or digested water/muck/waste produced with the small holding tanks 110 through the heat exchanger 156 before depositing it into the large holding tank 112. That exchange of heat energy is essential not only to complete the pasteurization process when pasteurization is necessary, but also to reduce the temperature of the heated and partially pasteurized or digested water/muck/waste mixture to 35-40° C. before it is deposited in the large holding tank 112.

That heated and partially pasteurized or digested water/muck/waste is pumped by a digester feed pump 132B that is controlled by the ECU 118 and operates to feed the heated and partially pasteurized or digested water/muck/waste into the large holding tank 112. That operation not only serves to pre-heat the water/muck/waste mixture before moving it to the small holding tanks 110, it beneficially removes heat from the heated and partially pasteurized or digested water/muck/waste before moving it to the large holding tank 112. As discussed below, the heated and partially pasteurized or digested water/muck/waste is preferably cooled down to about 40° C. before being depositing into the large holding tank 112.

The waste piping 136B through which the pre-heated water/muck/waste is moved to the small holding tanks 110 is preferably fitted within the floor of the container 102 so the buffer tank 108 can be drained from the bottom and the small holding tanks 110 can be fed from the bottom. If space does not permit and the small holding tanks 110 must be fed from the top, the feed tubes preferably extend to the bottom of the buffer tank 108 and/or each small holding tank 110 so that the mixture will be withdrawn from the bottom of the buffer tank 108 and/or deposited in the bottom of the small holding tanks 110. The buffer tank 108 is preferably sized to allow continuous operation of the REM apparatus 100 for at least 2 days. And it is preferably made out of steel or fiberglass to reduce manufacturing costs.

The buffer tank air sparge system (not depicted) is designed to ensure a certain level of oxygen to be present inside the buffer tank 108, to prohibit the production of biogas inside the tank through the process of anaerobic digestion. The air sparge system consists of a linear air pump that pumps air into an air-line. The air-line is led inside the tank to the base of the tank, where it forms a perforated loop that allows an even release of air. The linear air pump is electrically driven. It is sized to deliver sufficient air to inhibit the production of biogas and, in case any gas is produced, to sufficiently dilute these gases to prevent a flammable or explosive condition inside the tank.

The buffer tank overflow system 1118 is a safety measure to prevent overfilling of the buffer tank 108. It comprises a permanently non-obstructed discharge point 1118 at the top of the buffer tank 108, which may connect to the central drainage line 1116 of the command unit 902.

b. Small Holding Tanks 110

Returning to FIGS. 1A-1E, the pre-heated water/muck/waste is pumped from the buffer tank 108 to the small holding tanks 110 by a pasteurization feed pump 132C. That pump 132C operates on a predefined feeding cycle that is controlled by the ECU 118. In the small holding tanks 110, the pre-heated water/muck/waste is heated and stirred to produce pasteurization or, if pasteurization is not required for the overall anaerobic digestion process, to produce thermophilic anaerobic digestion. The pre-heated water/muck/waste in each small holding tank 110 is continuously stirred with a gas mixer 158 (FIG. 1E) to keep the solids and liquids in suspension during the pasteurization or thermophilic anaerobic digestion process. That mixture is heated with heaters 160 (FIG. 1E) capable of heating the mixture contained therein to around 55-75° C. The gas mixers 158 are pressurized with the compressor 128 and include nozzles that inject air directly into the bottom of each small holding tank 110 to promote aerobic thermophilic digestion, thereby supplementing the heating requirements during pasteurization. And the heaters 140 are either electric immersion heaters or water-based boiler-fed coil heaters that are disposed in the inside of the small holding tanks 110 so that the water/muck/waste mixture can be heated directly.

Each of the small holding tanks 110 has a relatively small volume (e.g., around 1,800 Liters) to reduce the energy required to heat the water/muck/waste disposed therein. Loads on the heaters 160 can be further reduced by recovering heat from the biogas engine 122 and/or the engines that drive the homogenizing pump 204, the de-watering unit 114, or any of the other pumps 132A-132D of the REM apparatus 100 in a regenerative manner so as to further increase the efficiency of the REM apparatus 100. And as discussed above, the small holding tanks 110 can be used to perform either pasteurization or thermophilic anaerobic digestion on the water/muck/waste disposed therein, depending on whether pasteurization is required for the overall anaerobic digestion process. If they are used to perform thermophilic anaerobic digestion, biogas will be generated in the small holding tanks 110 and similar precautions to those discussed below with respect to the large holding tank 112 will need to be taken (e.g., mixing the water/muck/waste with biogas instead of air, drawing off biogas to the gas storage tank, separating the small digester tanks 110 from machinery and electronics that may produce a spark, etc.). The small holding tanks 110 may also be used for other purposes, such as arresting the digestion process of the grey water in the liquor tank 126.

The small holding tanks 110 are operated in batch mode that includes offset cycles of feeding, holding, and discharge. For example, after the first small holding tank 110 is fed and filled with pre-heated water/muck/waste from the buffer tank 108, it will hold that pre-heated water/muck/waste while it is stirred and heated, as discussed above. The second small holding tank 110 will be fed and filled after the first small holding tank 110. The heated and partially pasteurized or digested water/muck/waste will then be discharged from first small holding tank 110 while the second small holding tank 110 holds, stirs, and heats the pre-heated water/muck/waste with which it was filled. And the heated and partially pasteurized or digested water/muck/waste will then be discharged from first second holding tank 110 while the second small holding tank 110 is filled with a new batch of pre-heated water/muck/waste from the buffer tank 108. Water/waste/muck is cycled through the small holding tanks 110 in that manner as required is repeated back and forth between the first and second digested tanks 110. The fill quantities are controlled by the ECU 118 using a set of level sensors (LS) in the small holding tanks 110. And although only two small holding tanks 110 are shown in FIGS. 1A-1E, the REM apparatus may use as many small holding tanks 110 are required to meet a user's processing demands.

The waste piping 136B through which the heated and partially pasteurized or digested water/muck/waste is moved to heat exchanger 136 in the buffer tank 108 is preferably fitted within the floor of the container 102 so that mixture can be fed up through the bottom of the buffer tank 108 so as to provide the proper temperature gradient (i.e., hottest on the bottom and coolest on the top) as the heated and partially pasteurized or digested water/waste/muck flows through the heat exchanger 156 in the buffer tank 108 and toward the large holding tank 112. Each small holding tank 110 is insulated to improve its efficiency. Preferably, the small holding tanks 110 are formed from PVC to reduce manufacturing costs and a "green" material, such as sheepswool, is used to form the insulation. The insulation can be formed in modular, interlocking pieces that can be connected together to surround the small holding tanks 110.

Additionally, the small holding tanks 110 may be used to process grey water piped in from the liquor tank 126. Similar to the pasteurization of the muck/waste, this process is designed to heat up the digestate/liquor from the liquor tank 126 to a specified temperature and to maintain it at that temperature for a specified amount of time (i.e. the pasteurization process) before it is off-loaded from the system. The REM apparatus 100 and 900 pasteurizes at a minimum temperature of 57° C. for a duration of five hours. These pasteurization characteristics are preferably compliant with quality and controlling storage requirements for feedstock, thus qualifying the pasteurized liquor as a sellable liquid fertilizer.

This embodiment of the small holding tanks 110 has two cylindrical, polypropylene tanks, each with a capacity of approximately 1,000 liters. The small holding tanks 110 are connected to the odor abatement system 908 through the odor abatement pipeline 1006, and are designed to be structurally sound and to prevent leakage of any material or gases. The tanks are insulated on all surfaces to reduce the transfer of thermal energy away from the contents. Each tank incorporates a man-hole to provide access to the inside of the tank for maintenance.

When full, the small holding tanks 110 are to be heated up to a minimum temperature of 57° C. and maintained at that temperature for five hours. Transfer of thermal energy into the contents of each small holding tank 110 is accomplished through an internal heat exchanger (not depicted), which consists of a stainless-steel coil that sits inside the small holding tanks 110 and allows the thermal energy of hot water (supplied from the CHP or boiler 922) to be transferred to the contents of the small holding tanks 110. The temperature is continuously measured via temperature sensors mounted inside the small holding tanks 110 and regulated via a pneumatically operated 3-port control valve that is automatically controlled by the main control system in reference to the sensor readings.

Each small holding tank 110 has a separate recirculation system 1114, designed to mix the content of the small holding tanks 110 and to prevent settling, separation or stratification of the liquor. Recirculation is provided through an electrically driven centrifugal pump 1114 mounted externally to the tank, with suction connected near the bottom of the tank and discharge 1108 connected towards the center level of the tank.

Each small holding tank 110 has a separate air sparge system 1123, designed to ensure a certain level of oxygen to be present inside the tanks to prohibit the production of biogas inside the tank through the process of anaerobic digestion. The air sparge system 1123 consists of a linear air pump that pumps air into an air-line. The air-line is led inside the tank to the base of the tank, where it forms a perforated loop that allows an even release of air. The linear air pump is electrically driven. It is sized to deliver sufficient air to inhibit the production of biogas and, in case any gas is produced, to sufficiently dilute these gases to prevent a flammable or explosive condition inside the tank.

The small holding tank 100 off-load system allows for pasteurized liquor—classifiable as liquid fertilizer, or fertilizer—to be off-loaded. The off-load system incorporates a single electrically driven centrifugal pump mounted 1104 externally to the tanks, with suction connected to both tanks. The discharge leads to a discharge point at the side of the command unit 902. At completion of an automated pasteurization cycle in a small holding tank 110, the HMI will indicate that the system is ready for fertilizer off-load. Starting the off-load procedure will cause the off-load pump 1104 to discharge the liquor to the off-load point at the side of the command unit 902. The off-load point is to be connected to the site-specific fertilizer off-load/storage facilities (e.g. disconnectable flexible hosing leading into storage containers).

The small holding tank drainage system 1110 is used when a small holding tank 110 needs to be emptied for maintenance purposes. The drainage system 1108 is connected from the bottom of each small holding tank 110 to the central drainage line 1116 of the command unit 902 via a manually operated ball valve.

c. Liquor Tank 126

The liquor tank 126 serves to hold the grey water, or liquor, that is separated from the muck/waste through the de-watering unit 114. The liquor tank can also be supplied liquor that is separated during any one of the various processes in components 106-128. The liquor tank 126 is used to store liquor until it is needed for the various processes in components 106-128. For example, the liquor tank can be used to feed liquor back into the chopper unit 106 to aid in the dilution process. The liquor from the liquor tank 126 can alternatively be used to supply liquor as needed to the buffer tank 108, small holding tanks 110, or the digester unit 904 to aid in their respective processes.

In the embodiment depicted in FIGS. 1A-1E, the liquor tank 126 is disposed adjacent to the first container 102 at a location near and below the de-watering tank 300 of the de-watering unit 114 so the solid fertilizer and liquid fertilizer produced with the de-watering unit 114 can be gravity fed into the liquor tank 126. To serve that purpose, the de-watering tank 300 is disposed on a base 308 that supports it at a location above the liquor tank 126. And although the liquor tank 126 is illustrated as being disposed adjacent to the first container 102, it may also be disposed inside the first container 102 in a similar relationship to the de-watering unit 114.

The liquor tank 126 may also be disposed adjacent to the first container 102. And although the anaerobic digestion process may take a few weeks to complete, after the first cycle is complete, there should be solid and liquid fertilizers ready to be extracted each time the user goes to load the chopper unit 106 with new muck/waste. The solid fertilizer may be mulch that is suitable for animal bedding. And at least a portion of the grey water may be re-circulated with the mixer feed pump 132A for mixture with muck/waste that is loaded into the mixing tank 132 as required for hydrolysis. The re-circulation of the grey water with the mixer feed pump 132A is controlled by the ECU 118 by automatically operating that pump 132A and opening/closing the associated water valves 134A as required to direct the flow of the grey water. The liquor tank 126 is preferably made of PVC to reduce manufacturing costs.

Figure 9A:
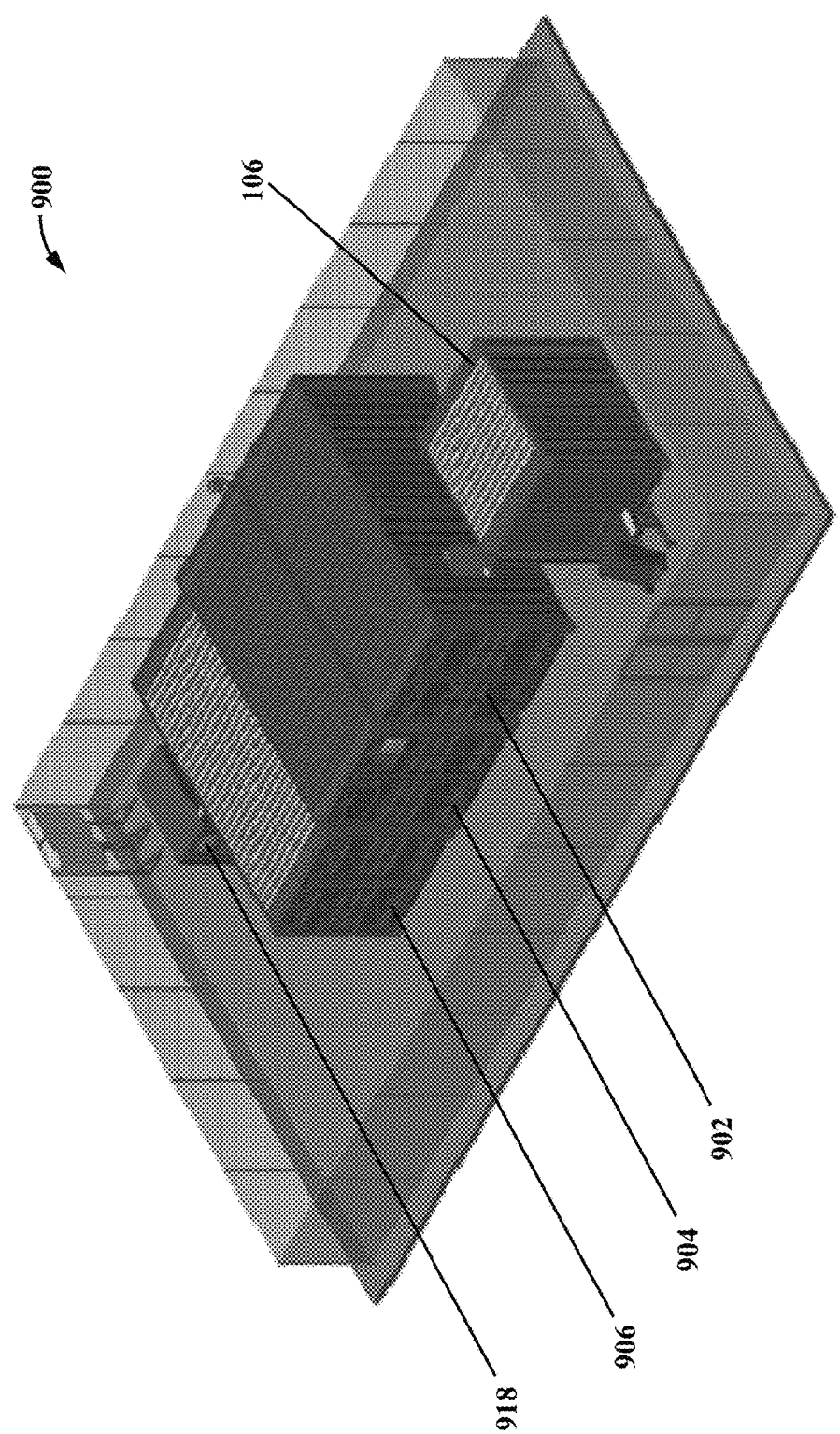
FIG. 9A is an isometric view that illustrates an example of an apparatus for renewable energy microgeneration according to another non-limiting embodiment of the present invention.
Figure 9B:
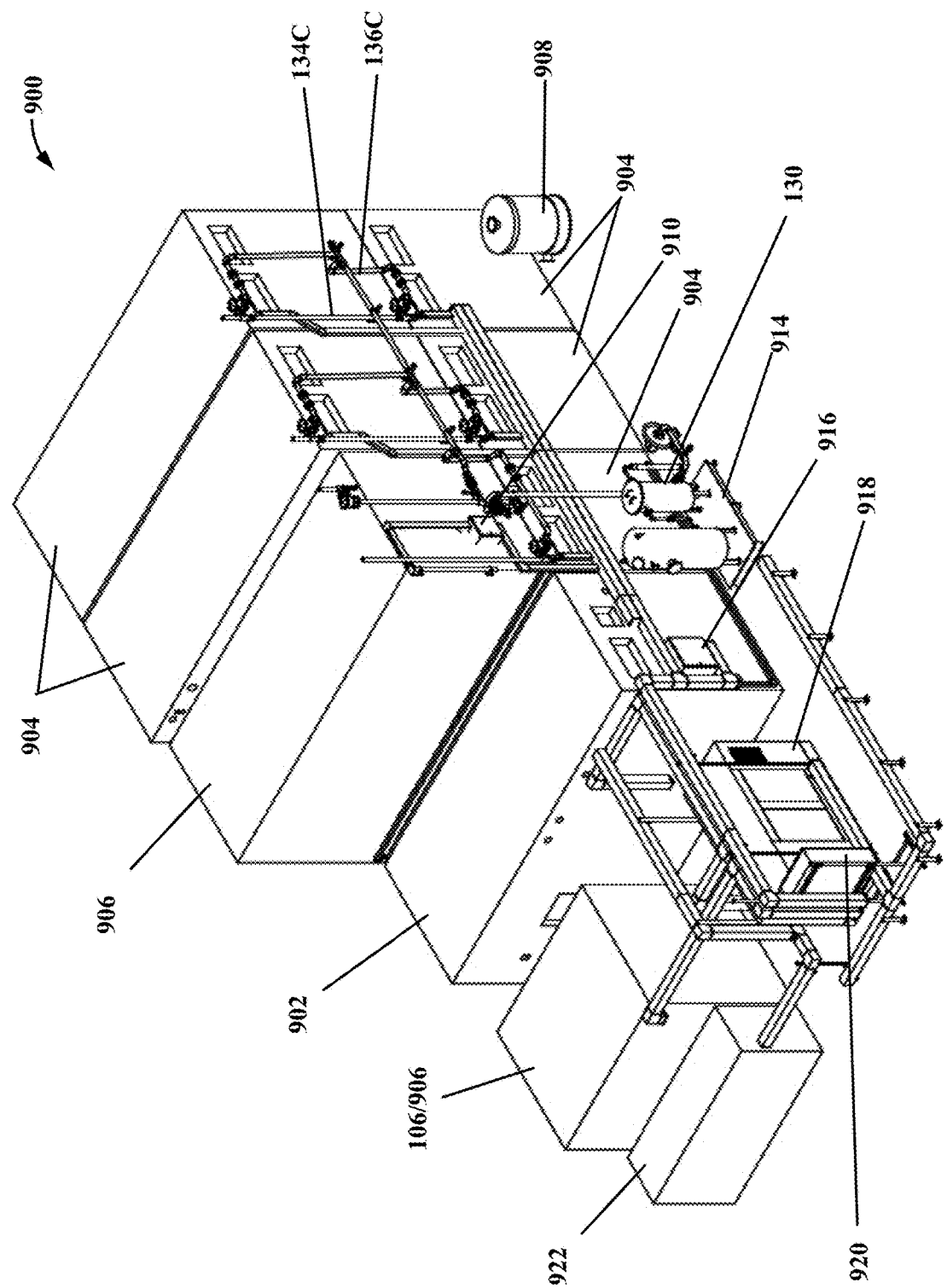
FIG. 9B is an isometric view that illustrates an example of an apparatus for renewable energy microgeneration according to another non-limiting embodiment of the present invention.
Figure 9C:
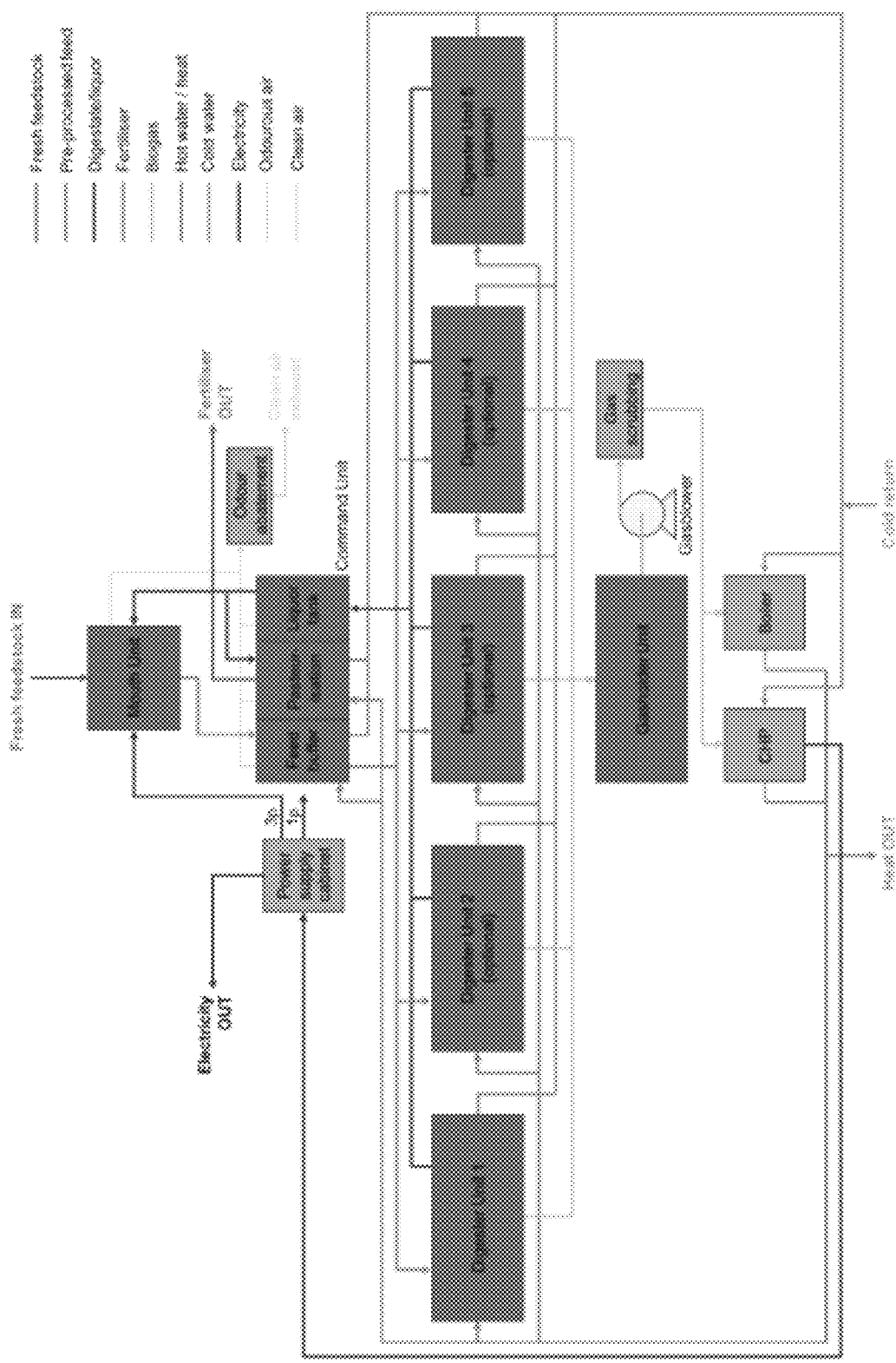
FIG. 9C is a schematic drawing that illustrates the apparatus of FIG. 9B.
Figure 11:
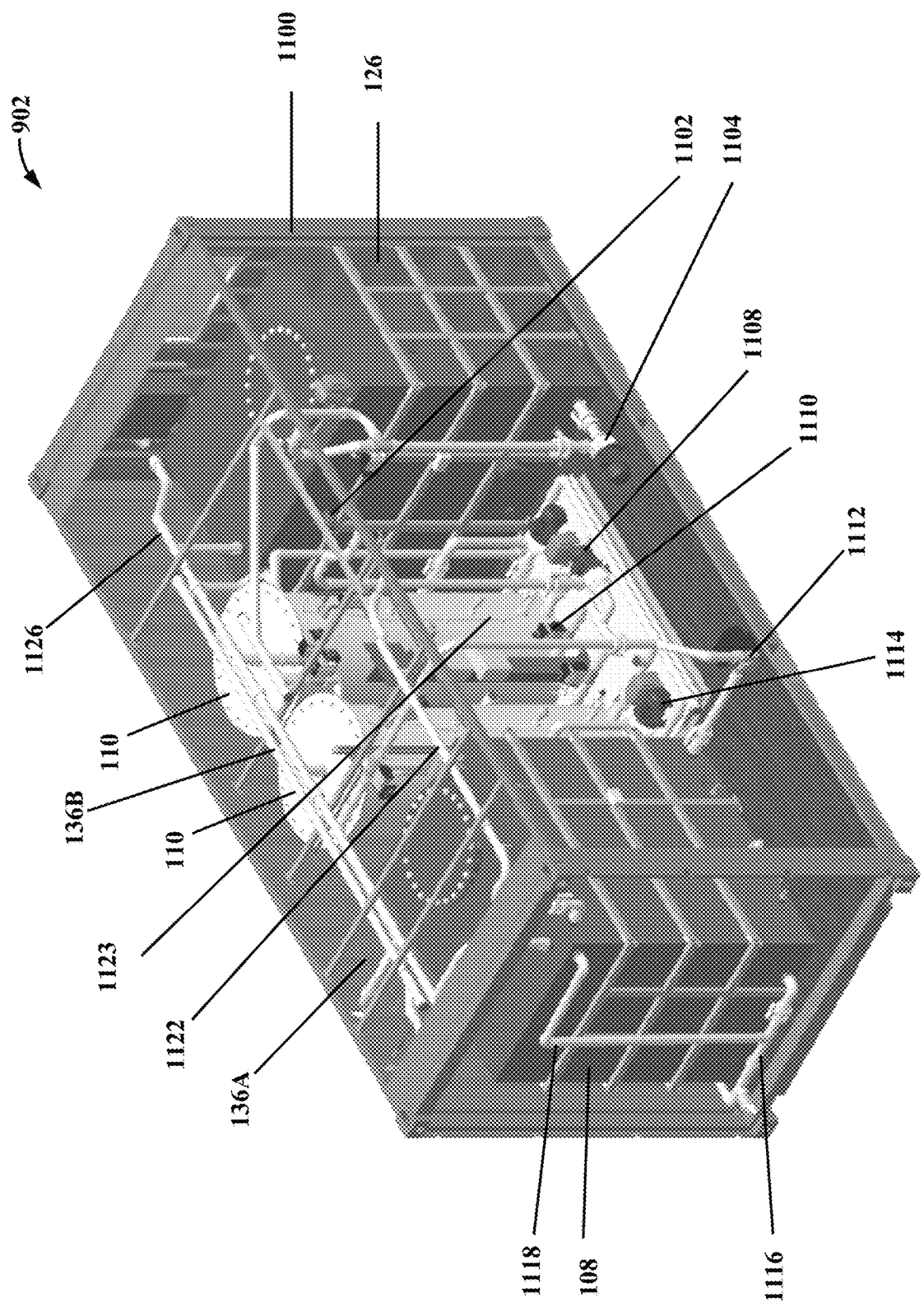
FIG. 11 is an isometric view that illustrates a command unit according to a non-limiting embodiment of the present invention depicted in FIGS. 9A and 9B.

In the embodiment depicted in FIGS. 9A, 9B, and 11, the liquor tank 126 is housed in a separate container called the command unit 902. The liquor tank 126 incorporates a man-hole for access to the inside of the tank for maintenance purposes. The liquor tank is connected to the odor abatement system 908 through the odor abatement pipeline 1006, and is designed to be structurally sound and to prevent leakage of any material or gases. It is manufactured from materials that provide resistance to corrosion and erosion for 20 years.

iv. Large Holding Tank 112

The heated and partially pasteurized or digested water/muck/waste is pumped from the small holding tanks 110 to the large tank 112 by the digester feed pump 132B. Like the pasteurization feed pump 132C, the digester feed pump 132B operates on a predefined feeding cycle that is controlled by the ECU 118. Because the heated and partially pasteurized or digested water/muck/waste must be cooled to approximately 40° C. before it is deposited in the large holding tank 112, it passes through the heat exchanger 156 in the buffer tank 108 as it is pumped from the small holding tanks 110 to the large tank 112. The heated and partially pasteurized or digested water/muck/waste is cooled by passing its heat energy to the water/muck/waste mixture in the buffer tank 108 via the heat exchanger 156, as discussed above. In that manner, the heat energy expended to support pasteurization or thermophilic anaerobic digestion in the small holding tanks 110 is re-used in a regenerative manner, thereby further increasing the efficiency of the REM apparatus 100.

In the large holding tank 112, the pasteurized or cooled and partially digested water/muck/waste is stirred to produce mesophilic anaerobic digestion. Like the pre-heated water/muck/waste in each small holding tank 110, the pasteurized or cooled and partially digested water/muck/waste in the large holding tank 112 is continuously stirred with a gas mixer 158 (FIG. 1E) to keep the solids and liquids in suspension while biogas (e.g., methane and carbon dioxide) accumulates at the top of the large holding tank 112. However, unlike the pre-heated water/muck/waste in each small holding tank 110, which is stirred with compressed air from the compressor 128, the pasteurized or cooled and partially digested water/muck/waste in the large holding tank 112 is stirred by re-circulating biogas through the gas mixer 158 using a corrosive gas vacuum pump 162. In the absence of air, bacterial populations break down organic solids in the water/muck/waste mixture into biogas and more stable solids. Thus, biogas is used to stir the water/muck/waste instead of air because introducing oxygen into that mixture would create an explosive atmosphere. In the alternative, a mixing pump (not shown) could be used to mix the water/muck/waste mixture by intermittently circulating it within large holding tank 112.

The operating temperature of the large holding tank 112 is preferably between 32-40° C. Those lower temperatures allow the large holding tank 112 be have a greater volume (e.g., around 14,000 Liters) than the small holding tanks 110 because less energy is required to maintain those lower temperatures. In fact, the large holding tank 112 may need to be cooled instead of heated. To serve that purpose, the large holding tank 112 may be made as a dual layer tank so that cooling fluid (e.g., potable and/or grey water) can be circulated between the inner and outer shells to cool the water/muck/waste disposed in the inner shell. The use of a conductive material, such as steel, on the inside shell and an insulating material on the outside shell provide a suitable way of achieving that functionality.

In the alternative, the large holding tank 112 may be formed as a single tank using low cost fiber reinforced thermoforms. That material allows a plurality of large holding tanks 112 to be rapidly manufactured using inexpensive molds. That material is also flexible so the large holding tanks 112 will not break if dropped when full of liquid (e.g., 1.5 meters full moving at 20 kph). In either embodiment, the large holding tank 112 may be painted with conditioned nanotech carbon in the shape of a lotus leaf to repel bacteria and with silicates to prevent methane from tunneling/leaking through tank walls. The large holding tank 112 is preferably immune to two types of bacteria—anammox bacteria and methagenic bacteria, which are used to eat both ammonia and to break down carbon chains. The large holding tank 112 may also include a cathode and anode that harvest free electrons from the digestion process so that the large holding tank 112 can be used as a big battery for powering the REM apparatus 100 or for providing power to other apparatus. The small holding tanks 110 may be similarly constructed.

The large holding tank 112 operates on a "draw and fill" mode where a known quantity of water/muck/waste is drawn into the large holding tank 112 by the digester feed pump 132C until it is filled to a pre-determined level. The draw and fill quantities are controlled by the ECU 118 using a set of level sensors (LS) in the large holding tank 112. The feed flowrate of water/muck/waste to the large holding tank 112 is controlled by the ECU 118 such that it provides a minimum retention time of 15 days for the mesophilic anaerobic digestion process. And during the draw down process, biogas is preferably drawn back into the large holding tank 112 from the gas storage tank 120 to maintain an operating pressure of 15-20 mbar within the large holding tank 112.

The large holding tank 112 is sufficiently sealed to prevent gaseous oxygen from entering the system and hindering the anaerobic digestion process. The large holding tank 112 includes a safety relief valve 164 that vents outside of the first container 102 and releases pressure from the large holding tank 112 if that pressure approaches unsafe levels. The large holding tank 112 is also insulated to improve its efficiency. Preferably, the outside shell of the large holding tank 112 is formed of fiberglass to reduce manufacturing costs and a "green" material, such as sheepswool, is used to form the insulation. The insulation can be formed in modular, interlocking pieces that can be connected together to surround the large holding tank 112.

As mesophilic anaerobic digestion is performed in the large holding tank 112, biogas collects at the top of the large holding tank 112. Although the pneumatic pump re-circulates some of that biogas back into the water/muck/waste as part of the mixing operation, the remainder of the biogas is drawn from the large holding tank 112 and pumped through the gas scrubber 116 before being deposited in the gas storage tank 120. That biogas is preferably discharged from the large holding tank 112 at an operating pressure of 15-20 mbar. And after the mesophilic anaerobic digestion process is completed, the digested water/muck/waste mixture is pumped to the de-watering unit 114 by a sludge draw-off pump 132D that is controlled by the ECU 118 based on the retention time required for the mesophilic anaerobic digestion process.

Because methane and other combustible gases are generated in the large holding tank 112, it may be necessary to provide it in a separate container from some of the other components of the REM apparatus 100—in particular, those components that contain moving machinery and electronics that may generate a spark (e.g., the chopper unit 106, the de-watering unit 114, the biogas engine 122, the air compressor 128, the mixer feed pump 132A, the digester feed pump 132B, the pasteurization feed pump 132C, the sludge draw-off pump 132D, the gas vacuum pump 162, and the homogenizing pump 204). In the alternative, a container can be divided into separate spaces using air-tight bulkheads to separate the large holding tank 112 from the machinery and electronics of the REM apparatus 100. Such a separate container or container space will preferably provide full hazardous material and explosive atmosphere separation from the machinery and electronics of the REM apparatus 100 in accordance with local, national, and/or international standards, such as the European Union's Atmospheres Explosibles (ATEX) directive and Dangerous Substances and Explosive Atmospheres Regulations (DSEARs).

Figure 12:
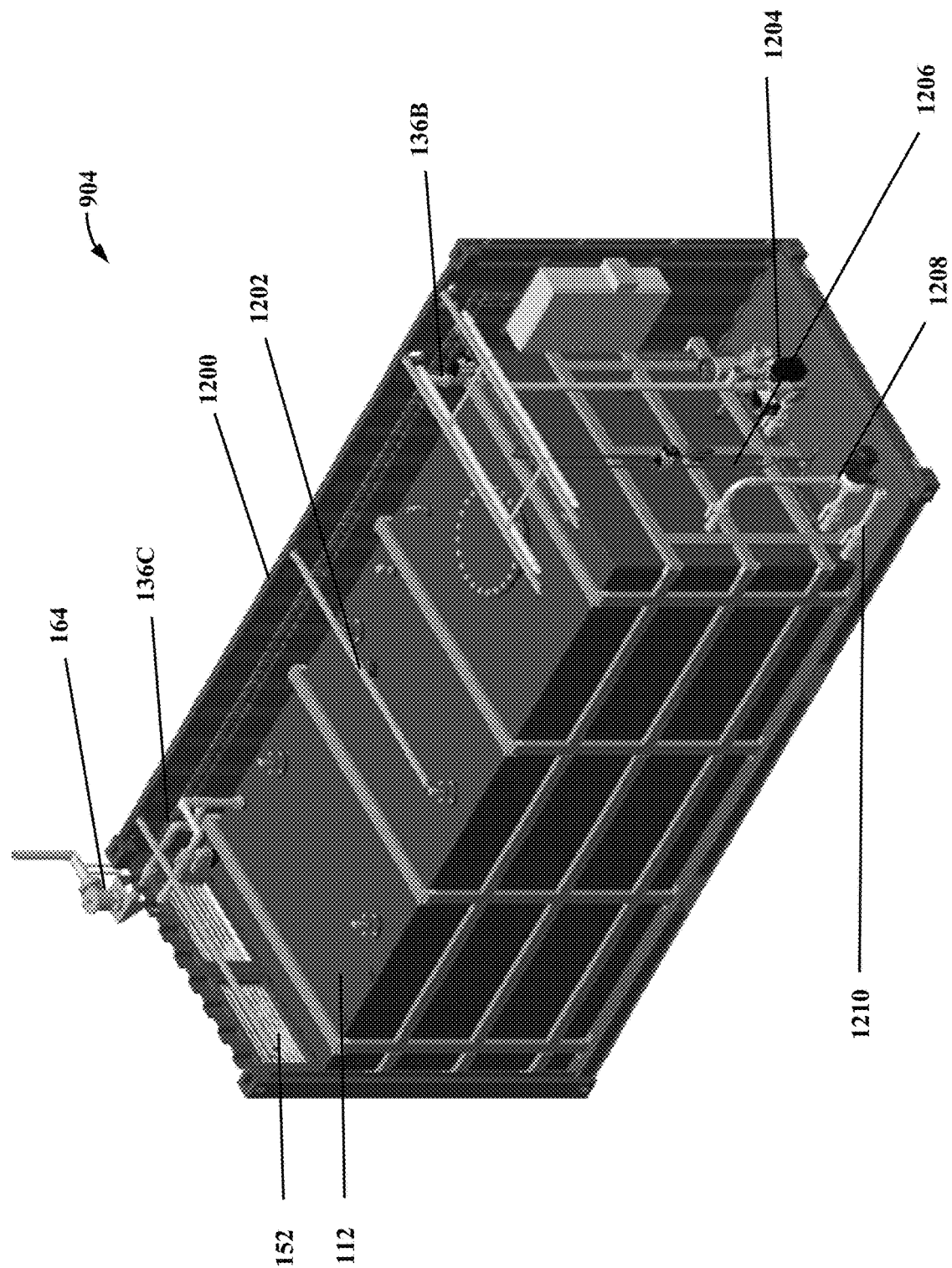
FIG. 12 is an isometric view that illustrates a digester unit according to a non-limiting embodiment of the present invention depicted in FIGS. 9A and 9B.

In the REM apparatus 100 and 900, the large holding tank 112 may be separated into its own 20-foot container, the digester unit 904, as depicted in FIGS. 9, 9B, and 12. This configuration provides the benefits described above of separating a combustible component from the rest of the REM apparatus 100 and 900. In one embodiment, the digester unit 904 has the capacity to store approximately 20,000 liters of digestate. This separate digester unit 904 also gives the system the ability to increase the number of digester units 904 while maintaining the same number of chopper units 106 and command units 902. In addition, various sensors may be moved to a panel on the front of the container 102 or 1000 to eliminate the need for ATEX sensors.

The buffer tank 108, the liquor tank 126, small holding tanks 110, and large holding tank 112 preferably are formed with conduit space in the corners to allow for interior piping and cable connection. Quick disconnections and pre-configured wiring harnesses may be accessed within this conduit space, which protects them from damage when installing and/or transporting these tanks 108, 110, 112, and 126 and/or their respective containers 102, 1100, and 1200. The buffer tank 108, the liquor tank 126, small holding tanks 110, and large holding tank 112 also preferably are formed with access hatches in the corners to allow access to the inside of the tanks 108, 110, 112, and 126 for performing maintenance. For example, the access hatches allow a user of the REM apparatus 100 or 900 to access the sensors located within the tanks 108, 110, 112, and 126.

v. De-Watering Unit 114

The de-watering unit 114 removes liquids from the fully digested water/muck/waste to produce a compost bi-product and thickened digestate that can be used as solid and liquid fertilizers. In certain instances, it may be desirable for the liquid removed from the fully digested water/muck/waste to have zero Chemical Oxygen Demand, or COD. Chemical Oxygen Demand is the total measurement of all chemicals in the water that can be oxidized. Accordingly, the de-watering unit 114 to be configured to achieve zero COD.

Figure 3:
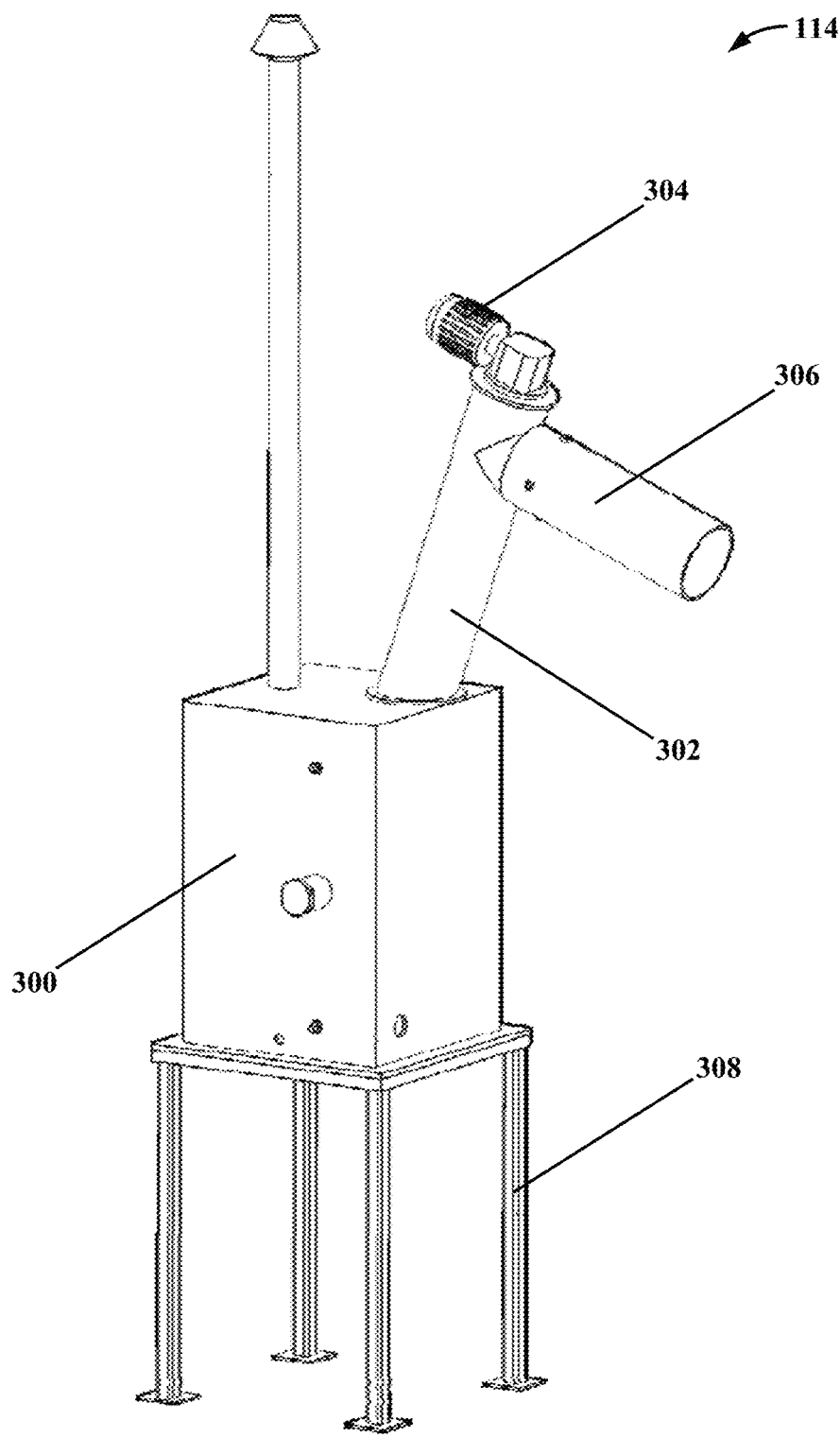
FIG. 3 is an isometric view that illustrates a de-watering unit according to a non-limiting embodiment of the present invention.

As FIG. 3 illustrates, the de-watering unit 114 includes a de-watering tank 300 where the digested water/muck/waste is received from the large holding tank 112. The de-watering unit 114 also includes a conveyor tube 302 and an electric motor 304 for rotating a shaftless screw conveyor disposed within the conveyor tube 302. As it rotates, the screw conveyor transports the solid muck/waste from the water/muck/waste mixture in de-watering tank 300 up through the conveyor tube 302 and out through a spout 306 disposed at the upper end of the conveyor tube 302. That solid muck/waste can be collected in a bin placed below the spout on the loading platform 142 for use as solid fertilizer. And the remaining grey water, or liquor, in the de-watering tank 300 is then gravity fed into the liquor tank 126 for use as liquid fertilizer.

The de-watering unit 114 may be disposed adjacent to the chopper unit 106 at the same end of the first container 102 so that the process of the present invention is completed at the same location it begins. Accordingly, the user can load muck/waste into the chopper unit 106 and extract the resulting solid fertilizer produced via the anaerobic digestion process at the same location. The liquor tank 126 may be disposed adjacent to the first container 102 at that same end for the same purpose. And although the anaerobic digestion process may take a few weeks to complete, after the first cycle is complete, there should be solid and liquid fertilizers ready to be extracted each time the user goes to load the chopper unit 106 with new muck/waste. The solid fertilizer may be mulch that is suitable for animal bedding. And at least a portion of the grey water may be re-circulated with the mixer feed pump 132A for mixture with muck/waste that is loaded into the mixing tank 132 as required for hydrolysis. The re-circulation of the grey water with the mixer feed pump 132A is controlled by the ECU 118 by automatically operating that pump 132A and opening/closing the associated water valves 134A as required to direct the flow of the grey water.

In the embodiment depicted in FIGS. 1A-1E, the liquor tank 126 is disposed adjacent to the first container 102 at a location near and below the de-watering tank 300 of the de-watering unit 114 so the solid fertilizer and liquid fertilizer produced with the de-watering unit 114 can be gravity fed into the liquor tank 126. To serve that purpose, the de-watering tank 300 is disposed on a base 308 that supports it at a location above the liquor tank 126. And although the liquor tank 126 is illustrated as being disposed adjacent to the first container 102, it may also be disposed inside the first container 102 in a similar relationship to the de-watering unit 114.

Figure 13:
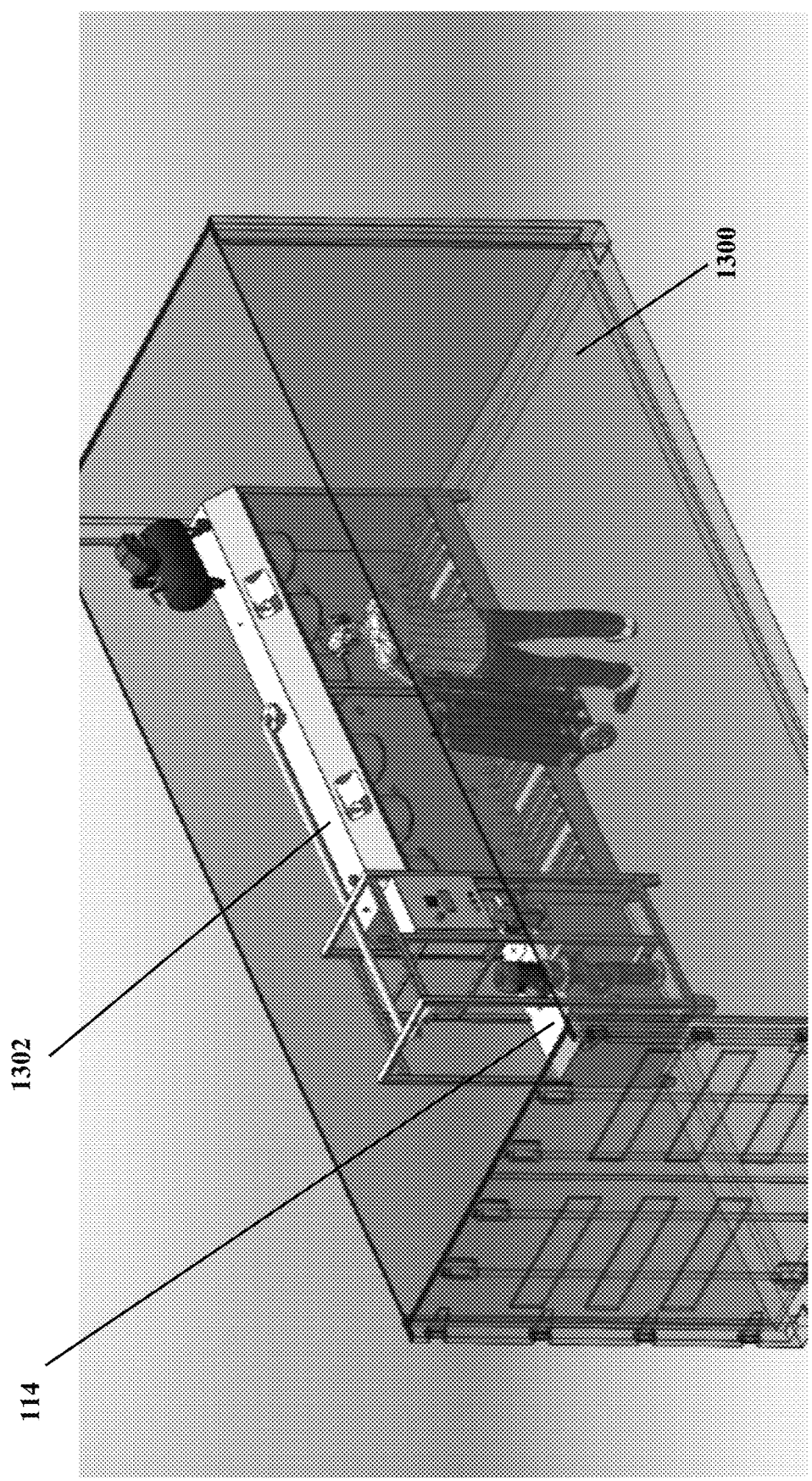
FIG. 13 is an isometric view that illustrates a de-watering unit with a bagging system according to a non-limiting embodiment of the present invention.

The de-watering unit 114 may also include a bagging system 1302 in a separate 20-foot container as depicted in FIG. 13. This bagging system 1302 automatically takes the solid waste/muck to be used as fertilizer from the de-watering unit 114 and deposits it into various standard sized bags for periodic removal. For example, the bagging system 1302 may automatically deposit solid waste/muck into 10 kg bags and convey them into 1 m³ pallets that can then be easily removed by a standard forklift and loaded onto a flatbed for transportation of site.

The bagging system 1302 is controlled by the ECU 118 and removes the need for manual unloading and packaging of the generated fertilizer. The container housing the bagging system 1302 may include level switches connected to the ECU 118 which monitor the container in order to avoid spillage. Additionally, the container may include grills/vents at the bottom of the container doors, and may include an extractor fan to provide circulation to minimize odor within the container. Alternatively, the bagging system 1302 may be attached to the odor abatement pipeline 1006 to remove odor from the container. In some embodiments, the dewatering unit 114 and the liquor tank 126 may be housed in the same container as the bagging system 1302.

vi. Salt Management and Removal System

Depending on the location and type of waste being processed, it may be necessary for the REM apparatus 100 or 900 to process significant amounts of salty food waste. The REM apparatus 100 or 900 therefore may include a salt management and removal unit. The salt management removal system relies on the various pumps and sensors in the various components of the REM apparatus 100 or 900 to monitor and control the salinity of the waste and the quality of biogas at various points during waste processing. It also includes software executed by the ECU 118 to control the flow of waste and grey water in a manner that maintains the optimal amount of salinity in the various processes occurring within the REM apparatus 100 or 900.

The salt management removal system includes one or more sensors in the buffer tank 108 measure salinity of the waste in the buffer tank 108 and one or more sensors in the large holding tank 112 to measure the salinity of the waste and the quality of biogas in the large holding tank 112. The ECU 118 compares the salinity measurements taken in the buffer tank 108 and the large holding tank 112 and compares them to a set value representing the salinity of ocean water. The ECU 118 monitors the differences in salinity of the inbound waste in the buffer tank 108 as compared to the salinity of waste being digested in the large holding tank 112. The ECU 118 also monitors the quality and volume of biogas in the large holding tank 112 and adjusts the inbound feed rate of waste from the buffer tank 108 to maximize biogas and methane production. There are a series of tables and self-learning algorithms in the software executed by the ECU 118 that adjust any, some, or all of the parameters of the various processes occurring within the REM apparatus 100 or 900 to maximize methane production in any given large holding tank 112.

After digestion in the large holding tank 112 is completed, excess digestate is offloaded to the liquor tank 126 before being pasteurized in one or more small holding tanks 110 and then offloaded to the dewatering unit 114 for further processing to remove salt.

In addition, while the coagulated solids in the dewatering unit 114 may not be salty, the separated water may contain excess salt. The salt management and removal unit therefore is configured to remove salt from the separated water through a reverse osmosis process, which yields both clean water and a salty brine. The clean water may be used as potable water, or it may be returned to the buffer tank 108 as required to dilute and/or reduce the salinity of incoming waste. The brine is dried into a solid using heat provided from the CHP, while the vapor created when drying the brine is captured as grey water that may be re-circulated to the mixing tank 132 by the mixer feed pump 132A.

vii. Gas Scrubber 116

The gas scrubber 116, or de-sulfurization unit, is disposed between the large holding tank 112 and the gas storage tank

120. It is configured to clean the biogas extracted from the water/muck/waste in the large holding tank 112 before it is stored in the gas storage tank 120. The gas scrubber 116 may be any suitable type, such as an activated carbon filter or a compressed gas filter (e.g., an amine gas filter). The gas scrubber 116 is used to treat the biogas and refine it for use as fuel—namely by reducing the levels of hydrogen sulfide in the biogas. However, the gas scrubber 116 may not be needed if the biogas does not need to be treated, such as when it is not going to be used for fuel or does not contain prohibited levels of certain chemicals.

viii. Electronic Control Unit (ECU) 118

Figure 4:
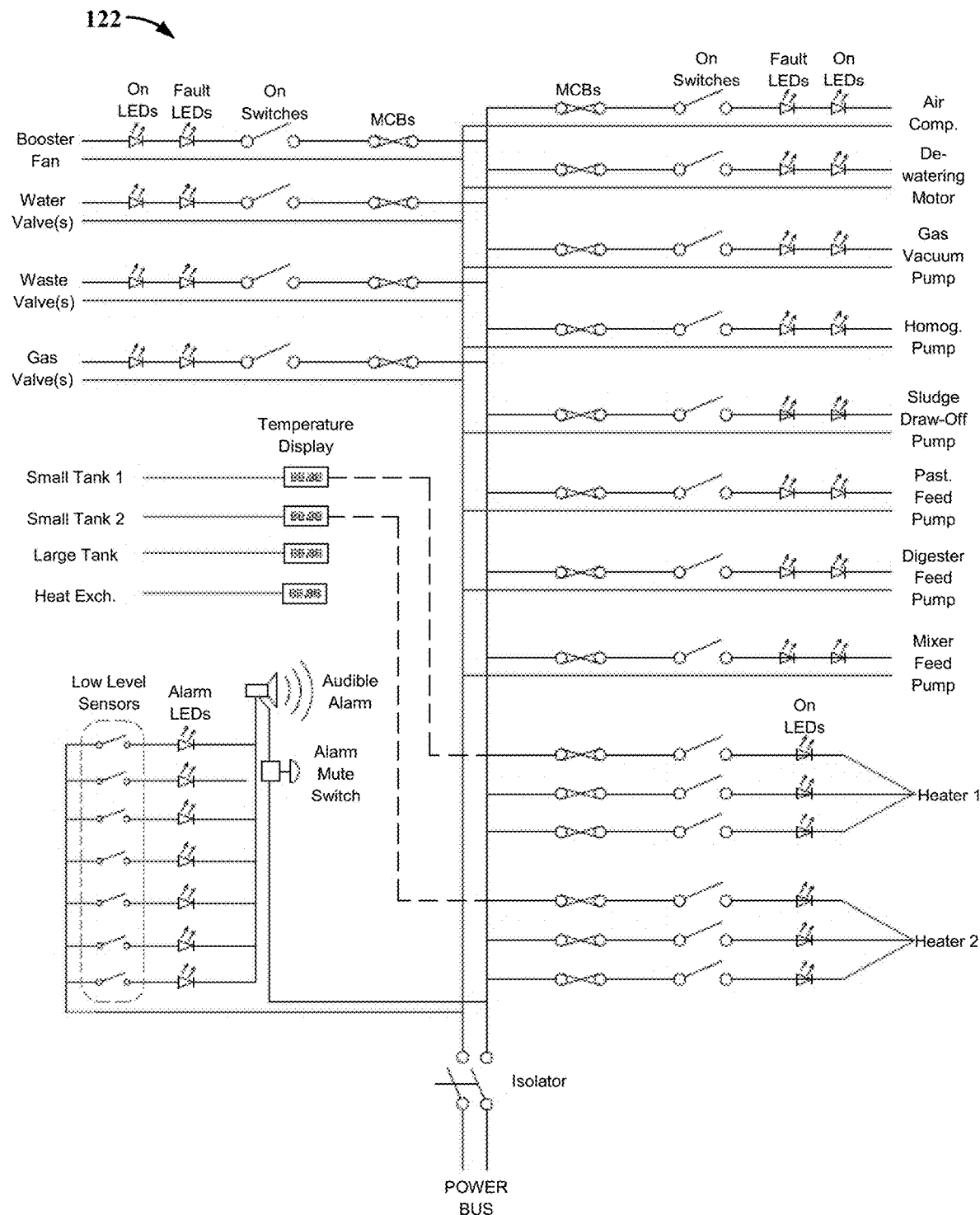
FIG. 4 is schematic diagram that illustrates a controller according to a non-limiting embodiment of the present invention.

The flow of liquid (e.g., potable and/or grey water), muck/waste, and biogas through the REM apparatus 100 of the present invention is controlled by the ECU 118. As FIG. 4 illustrates, the ECU 118 includes a programmable logic controller (PLC) that is programmed to monitor, record, and control the various stages of the anaerobic digestion process (e.g., temperatures, volumes, and flow rates). It provides visual feedback of those operations to the user via a graphical user interface, such as a computer monitor or touchscreen. The ECU 118 automates the anaerobic digestion process by turning the various components 106-128 of the REM apparatus 100 on and off based on the values it monitors and records. The ECU 118 makes the determination as to which components 106-128 to turn on and off primarily based on the content of the muck/waste loaded into the REM apparatus 100, which can be detected with the appropriate sensors and/or can be input by a user via a user interface at the ECU 118.

For example, the ECU 118 will automatically operate the appropriate pumps 132A-132D, 204, and 162 and open/close the appropriate valves 134A-134C to pump the fully digested water/muck/waste from the large holding tank 112 to the de-watering unit 114 after it detects that the anaerobic digestion process is completed. The ECU 118 will automatically feed, hold, and discharge water/muck/waste from the small holding tanks 110 in batch mode based on levels detected with level switches (LS) and the times over which the water/muck/waste has been held in each small holding tank 110. The ECU 118 will determine whether or not to activate the heaters 160 in the small holding tanks 110 based on temperature sensors (TS) in each small holding tank 110. And the ECU 118 will automatically determine the flow rates and cycle times for moving the water/muck/waste between the different components 106-128 of the REM apparatus 100 by monitoring the anaerobic digestion process in its various stages using a clocking circuit, level sensors (LS) temperature sensors (TS), and pressure sensors (PS) located throughout the REM apparatus 100, thereby allowing the ECU 118 to adjust the anaerobic digestion process in real time as required to maintain optimal digestion.

The ECU 118 can determine such things as the amount of liquid to add to the muck/waste mixture and the amount of biogas expected to be produced from that muck/waste based on the answers to a series of questions presented to the user via the graphical user interface of the ECU 118. For example, the user could be asked to input a description of the site where the muck/waste was collected, the availability of services, waste/muck type (e.g., manure, vegetable waste, etc.), waste/muck quantities, the intended use of the mulch that will be produced, and the intended use of the grey water that will be produced. Thus, by allowing a user to input the answers to those questions for different batches of muck/waste loaded into the REM apparatus 100, the ECU 118 is able to customize the digestion process for each batch of muck/waste loaded into the REM apparatus 100. Some of those answers may also be obtained automatically by the ECU 118, such as using a scale provided on the chopper unit 106 or the loading platform 142 to weigh the muck/waste loaded into the REM apparatus 100.

The PLC of the ECU 118 is also programmed to monitor and maintain safety throughout the anaerobic digestion process. That monitoring not only allows close control of machinery and electrical equipment to prevent physical injury to users, it also allows close control the process parameters that are used as Hazard Assessment and Critical Control Parameters (HACCPs). For example, the ECU 118 monitors the biogas pressure in the gas storage tank 120 and the levels of water/muck/waste in the small holding tanks 110 and large holding tank 112 to make sure they are maintained at safe operating levels (e.g., a level sensor (LS) will be provided in the small holding tanks 110 and large holding tank 112 to ensure that the immersion heaters 160 are not trying to heat an empty tank). Alarms will sound if/when the volumes of biogas and/or volumes of water/muck/waste approach unsafe levels. The ECU 118 also includes a supervisory control and data acquisition (SCADA) interface and/or Internet and wireless (e.g., GSM, GPRS, wifi, etc.) functionality for providing the user with remote monitoring capabilities for efficiency, diagnostics, operations, and safety. Preferably, the ECU 118 is provided at the same end of the first container 102 as the chopper unit 106, de-watering unit 114, and liquor tank 126 so the anaerobic digestion process can be controlled from the same location that muck/waste is loaded into the REM apparatus 100 and fertilizer is removed from the REM apparatus, thereby providing an added level of convenience to the user.

The ECU 118 includes a human-machine interface (HMI) for communicating with the various components 106-128, pumps 132A-132D, and valves 134A-134C of the REM apparatus 100. It also includes a cloud monitoring application for regionally monitoring the status of those components 106-128, pumps 132A-132D, and valves 134A-134C.

Communication can be established with the ECU 118 via the SCADA interface and/or Internet and wireless functionality using substantially any computing device (e.g., personal computer, laptop computer, tablet computer, personal digital assistant (PDA), smart phone, etc.) so as to allow a user to remotely monitor, control, and troubleshoot the REM apparatus 100. For example, smart phone applications can communicate with the ECU 118 via a bus interface to a canbus node that communicates to low cost sensors and devices, such as those used in the automotive industry.

All of the interfaces for a user to input information into and otherwise control the operation of the ECU 118 are provide in the control box 148 located on the facia 140 of the first container 102 so the user can operate the different components 106-128 of the REM apparatus 100 from the same location where muck/waste is loaded into the REM apparatus 100 and solid and liquid fertilizers are removed from the REM apparatus 100, thereby adding an additional level of convenience to the user. The control box 148 and its associated interfaces are in electrical data communication with the ECU 118 via electrical wiring 138. Or in the alternative, they may be in wireless data communication with each other via any suitable, secure wireless functionality (e.g., GSM, GPRS, wifi, etc.).

The ECU 118 also provides a central source of power for the various components 106-128, pumps 132A-132D, and valves 134A-134C of the REM apparatus 100. It includes a miniature circuit breaker (MCB) for each of those components 106-128, pumps 132A-132D, and valves 134A-134C as well as light emitting diodes (LEDs) that indicate their respective status (e.g., "on", "fault", etc.). Those MCBs may are accessible via a breaker box 166 (FIG. 1A) disposed on the outside of the first container 102. The breaker box 166 is disposed on the outside of the first container 102 so that those MCBs can be easily accessed without needing to go into the container 102 where the risks of user injury are higher due to the amount of machinery housed therein. The other components of the ECU 118 are preferably disposed in an enclosure inside the first container 102 to provide better protection from the elements.

The power bus of the ECU 118 preferably receives its power from a 16 amp, 240 volt mains power supply. It may also receive its power from the biogas engine 122. And although FIG. 5 only shows four temperature sensors (TS) and seven "low" level switches (LS), the ECU 118 is connected to several other temperature sensors (TS) and level sensors (LS) to support its control of the REM apparatus 100. For example, the ECU 118 also includes at least seven "high" level sensors (LS) and at least three additional temperature sensors (TS). See, e.g., FIG. 1E. The ECU 118 may also be connected to other types of sensors, such as gas composition sensors, pressure sensors (PS), voltmeters, etc., as required to support its control of the REM apparatus 100. The wiring 138 of the ECU 118 and its various connections are compliant with the local, national, and/or international standards, such as those set forth in the Water Industry Mechanical and Electrical Specification (WIMES).

The ECU 118 may also be connected to a smart grid interface system to allow switching between heating and power sources. For example, the ECU 118 may be connected to solar electric thermal panels to provide heat and power to various components in the REM apparatus 100. The ECU 118 may switch between power and heating sources during operation as determined by the various sensors throughout the REM apparatus 100.

ix. Gas Storage Unit 906

Figure 5:
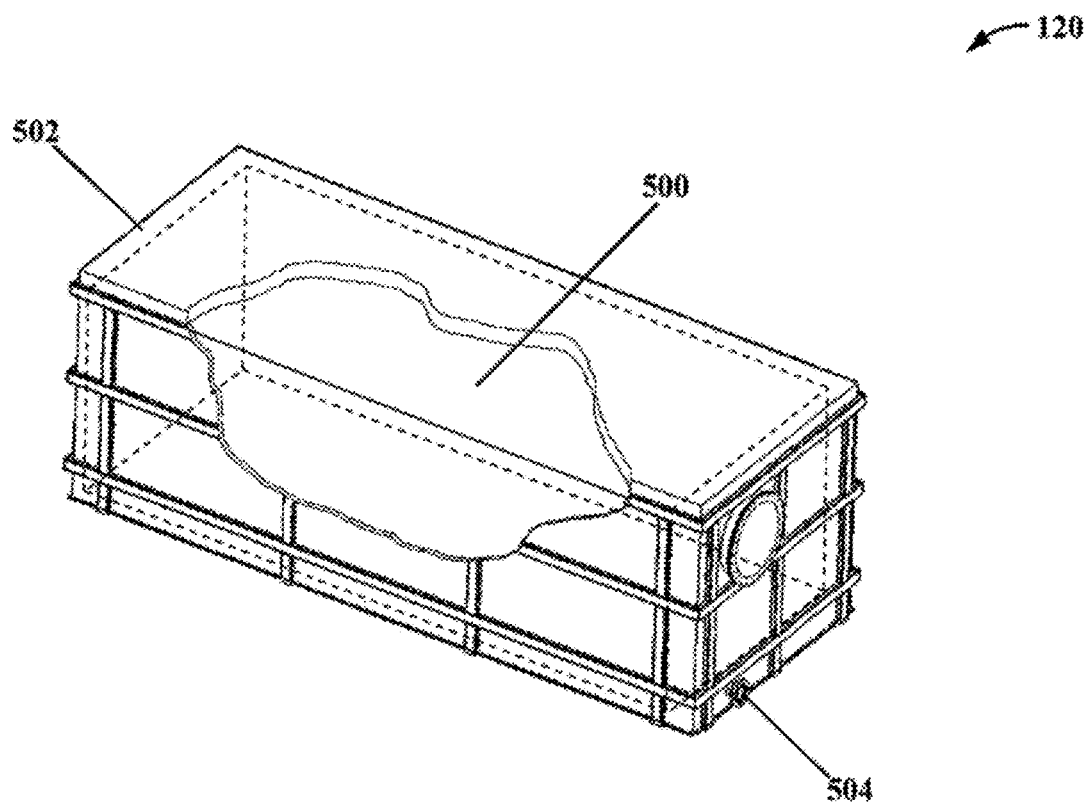
FIG. 5 is an isometric cutaway view that illustrates a gas storage tank according to a non-limiting embodiment of the present invention.

After the biogas is extracted from the large holding tank 112, and after it is cleaned by the gas scrubber 116 (when cleaning is required), it is stored in the gas storage tank 120 of the gas storage unit 906. As FIG. 5 illustrates, the gas storage tank 120 includes a flexible bladder 500 disposed inside a solid, double-walled tank 502. The double-walled tank 502 may be filled with liquid (e.g., potable and/or grey water) and constructed of a sufficiently strong material to withstand the high pressures associated with storing the biogas under pressure. The gas storage tank 120 includes a water inlet 504 and a water outlet (not shown) so the liquid can be pumped into and out of the double-walled tank 502 via water piping 136A to equalize and maintain a constant, fixed pressure of biogas in the flexible bladder 500. The gas storage tank 120 also includes a safety relief valve 168 that vents outside of the second container 104 and releases pressure in the flexible bladder 500 if that pressure approaches unsafe levels. Any surplus biogas that cannot be stored by the gas storage tank 120 is safely burned off with the flare 124 so as to prevent unsafe levels of pressure occurring. That flare 124 has a pilot light that is powered by a propane tank 170 provided in or adjacent to the first container 102. The flare 124 also may have a water jacket (not depicted) that is fed with water from the system for use in heat absorption and boiling water, as discussed above.

To measure the volume of gas stored in the flexible bladder 500, a separate flow meter is provided at the inlet and outlet gas piping 136C of the gas storage tank 120. The difference between the readings at those flow meters is used by the ECU 118 to monitor the amount of gas stored in the gas storage tank 120. Also provided at the outlet gas piping 136C is a flow control valve 134C for controlling the flow of biogas from the gas storage tank 120 and a flame arrestor (not shown) for preventing a flame from propagating back through the flow control valve 134C into the gas storage tank 120. In that way, biogas can be extracted from the gas storage tank 120 as needed and used to generate heat, electricity, or any other form of gas-generated energy. One of the devices that is used to generate heat and electricity is the biogas engine 122.

Because methane and other combustible gases are stored in the gas storage tank 120, it may be necessary to provide it in a separate container 104 from some of the other components of the REM apparatus 100 or 900—in particular, those components that contain moving machinery and electronics that may generate a spark (e.g., the chopper unit 106, the de-watering unit 114, the biogas engine 122, the air compressor 128, the mixer feed pump 132A, the digester feed pump 132B, the pasteurization feed pump 132C, the sludge draw-off pump 132D, the gas vacuum pump 162, and the homogenizing pump 204). In the alternative, a container can be divided into separate spaces using air-tight bulkheads to separate the large holding tank 112 from the machinery and electronics of the REM apparatus 100. Such a separate container or container space will preferably provide full hazardous material and explosive atmosphere separation from the machinery and electronics of the REM apparatus 100 or 900 in accordance with local, national, and/or international standards, such as the European Union's ATEX directive and DSEARs. The gas storage tank 120 container 104, as designed, will have been tested and validated to withstand an explosion of a full gas storage tank 120 pursuant to the theoretical explosion calculations of such standards. Preferably, all of the containers 102, 104, 1000, 1100, 1200, and 1300 will have been tested and validated to these standards to ensures that the gas storage tank 120, and indeed the entire REM apparatus 100 and 900, are safe to use in population centers such as inside large city buildings.

As a further safety measure, each of the containers 102, 104, 1000, 1100, 1200, and 1300 also preferably includes one or more pressure relief devices (not depicted), such as pressure relief discs, that will release pressure within the container 102, 104, 1000, 1100, 1200, or 1300 before it reaches unsafe levels. For example, pressure relief discs could be connected to the ECU 118 so that a signal is generated when a pressure relief bursts, which would alert the operator of the REM apparatus 100 or 900 that pressure within one or more of the containers 102, 104, 1000, 1100, 1200, and 1300 was approaching unsafe levels.

The gas storage unit 906 also may include a system to separate carbon dioxide from methane (not depicted). The carbon dioxide extraction system uses various catalysts, combined with steam, to separate the carbon dioxide and methane. This separated carbon dioxide may be fed back into the digester unit 904 to aid the mixing process. The use of carbon dioxide, when combined correctly in the digester unit 904 or in the large holding tank 112, enhances the anaerobic digestion and mixing process instead of using biogas, as others in industry use it, to mix their digesters. The ECU 118 controls the mixing to manage the parasitic load of the system and the release of biogas. Continuous mixing is beneficial for a huge parasitic load, while no mixing causes the system to produce less biogas because fluid density prevents gas release.

Several different carbon dioxide separation systems can be used within the REM apparatus 100 and 900. One optional unit for carbon dioxide separation is a three-stage compression system with a pump and vessel at each stage, such that first pumping stage causes the sulfurous gasses to liquefy, the second stage liquefies carbon dioxide, and the third stage performs compression. At each stage, the storage vessel may include a bleeding line that allows the liquified gas to be released from the combined vessel into another container for export. The liquified gas in the storage vessels may also be recycled, through the bleeding line, by pumping the liquified gas into the digester for mixing. The liquified gas in the storage vessels may also be collected as a crude unrefined gas to be used elsewhere, such as in greenhouses to increase plant productivity, as understood by experts in the greenhouse trade.

The gas storage unit 906 also may incorporate a gas compression unit (not depicted) that compresses the biogas before it is stored in the gas storage tank 120. Alternatively, the gas compression unit can be used to compress excess biogas into separate storage units or standardized, portable compressed gas containers for use in mixing, as described above, or for use with other systems. This compression allows the gas storage unit 906 to hold significantly more biogas, which allows the REM apparatus 100 or 900 to operate for several days with only a single gas storage tank 120.

x. Biogas Engine 122

The outlet gas piping 136C from the gas storage tank 120 is connected to the biogas engine 122, which simultaneously produces electricity and heat from the biogas via a combustion engine (e.g., an internal combustion engine or a Stirling engine). The biogas engine 122 is sized ranging from a 5 kwhe to 50 kWhe combined heat and power (CHP) unit. The CHP unit can be a modified diesel genset that burns biogas or a pyrolsis-based syngas/biogas burning steam engine (e.g., a sterling format, a rotary piston engine, or an opposed piston engine that drives a generator directly). In another embodiment, the biogas engine can be a fuel cell module, with or without a steam reformer, designed to use the methane rich biogas. At its most complete, the CHP is a trigen system which produces electricity, recovers the heat, and produces cooling. This system may have a heat storage unit to collect heat from either the solar thermo/electric panel or the biogas engine 122.

Because the biogas engine 122 requires a specific input pressure to operate (e.g., 100 mbar), biogas is maintained in the gas storage tank 120 at that pressure using a booster fan 172. The electricity produced with the biogas engine 122 can be linked to the user's power grid and used to power household devices, such as lights and appliances. And the heat produced can be linked to the user's heating, ventilation, and air conditioning (HVAC) system and/or water heating system and used for space heating and/or water heating. The biogas engine 122 may also be used to power the various pumps 134A-134D, 204, and 162 of the REM apparatus, or any component 106-128 that runs on electricity, and to provide heat to the small holding tanks 110 to further improve the efficiency of the present invention.

To further the mobility of the REM apparatus 100, the biogas engine 122 is preferably provided on its own trailer. It is also preferably connected to the gas storage tank 120, the power bus of the ECU 118, and a user's power grid using standard connections.

In another embodiment, the biogas engine 122 may be used in conjunction with, or replaced with, a natural gas boiler system 922. The natural gas boiler 922 operates similarly to the biogas engine 122 in that it processes the biogas to generate electricity and heat. This boiler operates similarly to common natural gas boilers, though it may be modified to specifically process the biogas generated through the REM apparatus 100 and 900 more efficiently. In one embodiment, the natural gas boiler would use a heat-jacketed flare 124 to boil water to generate electricity and heat for the REM apparatus 100 and 900.

xi. Flare 124

The flare 124 produces flame that burns surplus methane and/or propane to the European Union's particulate standard. The flare 124 includes a pilot light that is connected to the propane tank 170 via gas piping 134B to ensure that surplus biogas is instantly lit and remains lit so it does not gather in unsafe, combustible amounts in and/or around the REM apparatus 100. The flare may include two separate pilot lights—a first pilot light that burns methane and a second pilot light that burns propane. A piezoelectric lighter or an auto ignition system with visual flame detection may also be used and integrated with the functionality of the ECU 118 for automated triggering.

In another embodiment, the REM apparatus may use the biogas engine 122 or the natural gas boiler 922 in place of the flare 124, or in addition to the flare 124. The natural gas boiler 922 takes the surplus methane and/or propane from the various systems and uses it to create CHP to power the REM apparatus 100 or 900, rather than simply burning off the excess biogas using the flare 124. Accordingly, the flare 124 may be optional in certain configurations. The flare 124 also may be optional in configurations that include the odor abatement system 908 disclosed in more detail below.

xii. Piping 136A-136C a. Water Piping 136A

Figure 6:
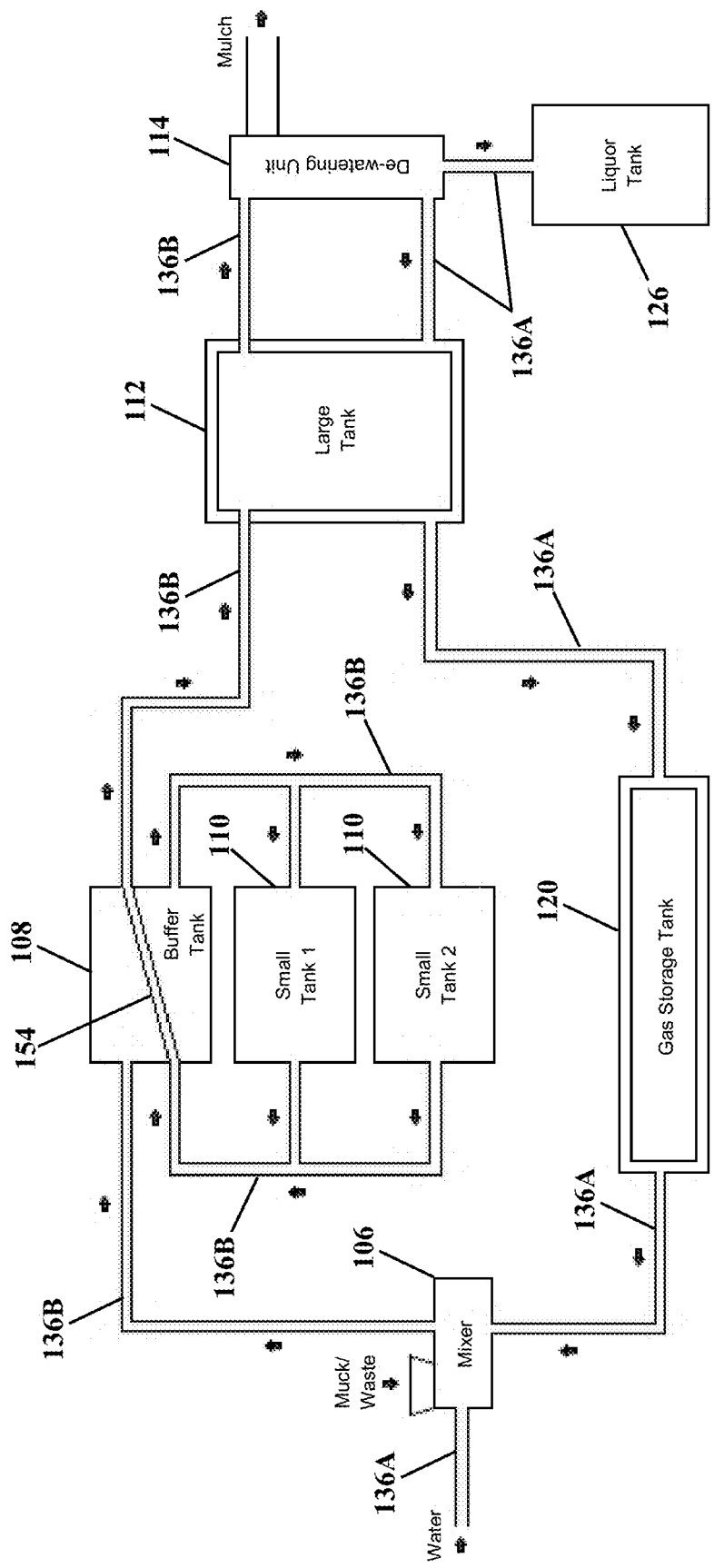
FIG. 6 is schematic diagram that illustrates water and waste piping according to a non-limiting embodiment of the present invention.

The water piping 136A may be any suitable low-pressure piping, such as PVC piping, for feeding liquid (e.g., potable and/or grey water) into the chopper unit 106. As FIG. 6 illustrates, the water piping 136A delivers potable water to the chopper unit 106 from an outside water source, such as a well or a local utility, and delivers grey water to the chopper unit 106 from the de-watering unit 114. To allow the REM apparatus 100 to be connected to an outside water source, the water piping 136A preferably includes a standard connector, such as a garden hose connector, at an inlet location on the outside of the first container 102.

As FIG. 6 also illustrates, the grey water from the de-watering unit 114 is circulated between the inner shell and outer shell of the large holding tank 112 and between the outer shell and the bladder of the gas storage tank 120 to aid in the cooling of the contents of the large holding tank 112 and the gas storage tank 120. The ECU 118 controls the amount of cooling provided as required to maintain the desired operating temperatures in the large holding tank 112 and the gas storage tank 120 by opening and closing the appropriate water valves 134A and operating the mixer feed pump 132A. And although FIG. 6 shows grey water being pumped through both the large holding tank 112 and the gas storage tank 120, one or both of those components 112 and 120 can be bypassed by opening and closing the appropriate water valves 134A.

b. Waste Piping 136B

The waste piping 136B provides a complex network that works its way around the fixed components 106-128 of the REM apparatus 100. Standard pipe lengths are used where possible to facilitate ease of manufacturing. The material used for the waste piping 136B is preferably HDPE. The properties of that material allow it to withstand chemical and biological attack, to withstand temperatures up to 137° C., and to withstand pressures up to 12 bar. Moreover, its insulating properties help further improve the efficiency of the REM apparatus 100. A standard drain connection is preferably provided on the outside of the first container 102 to facilitate connecting the waste piping 136B to a sump for draining the buffer tank 108, small holding tanks 110, large holding tank 112, liquor tank 126, mixing tank 202, and de-watering tank 300 as required to clean and maintain them.

As FIG. 6 also illustrates, the waste piping 136B delivers the water/muck/waste mixture to the buffer tank 108 before delivering it to the small holding tanks 110. Then, the heated and partially pasteurized or digested water/muck/waste mixture passes through the heat exchanger 156 in the buffer tank 108 as it is moved from the small digesters tanks 110 to the large holding tank 112. And after mesophilic anaerobic digestion is completed in the large holding tank 112, the fully digested water/muck/waste mixture is moved to the de-watering unit 114. The ECU 118 controls the amounts water/muck/waste moved between those components 106-114 as required to optimize the anaerobic digestion process by opening and closing the appropriate waste valves 134E and operating the digester feed pump 132B, the pasteurization feed pump 132C, the sludge draw-off pump 132D, and the homogenizing pump 204. And although FIG. 6 shows the heated and partially pasteurized or digested water/muck/waste mixture being pumped through the heat exchanger 156 in the buffer tank 108, the heat exchanger 156 can be bypassed by opening and closing the appropriate waste valves 134B.

c. Gas Piping 136C

Figure 7:
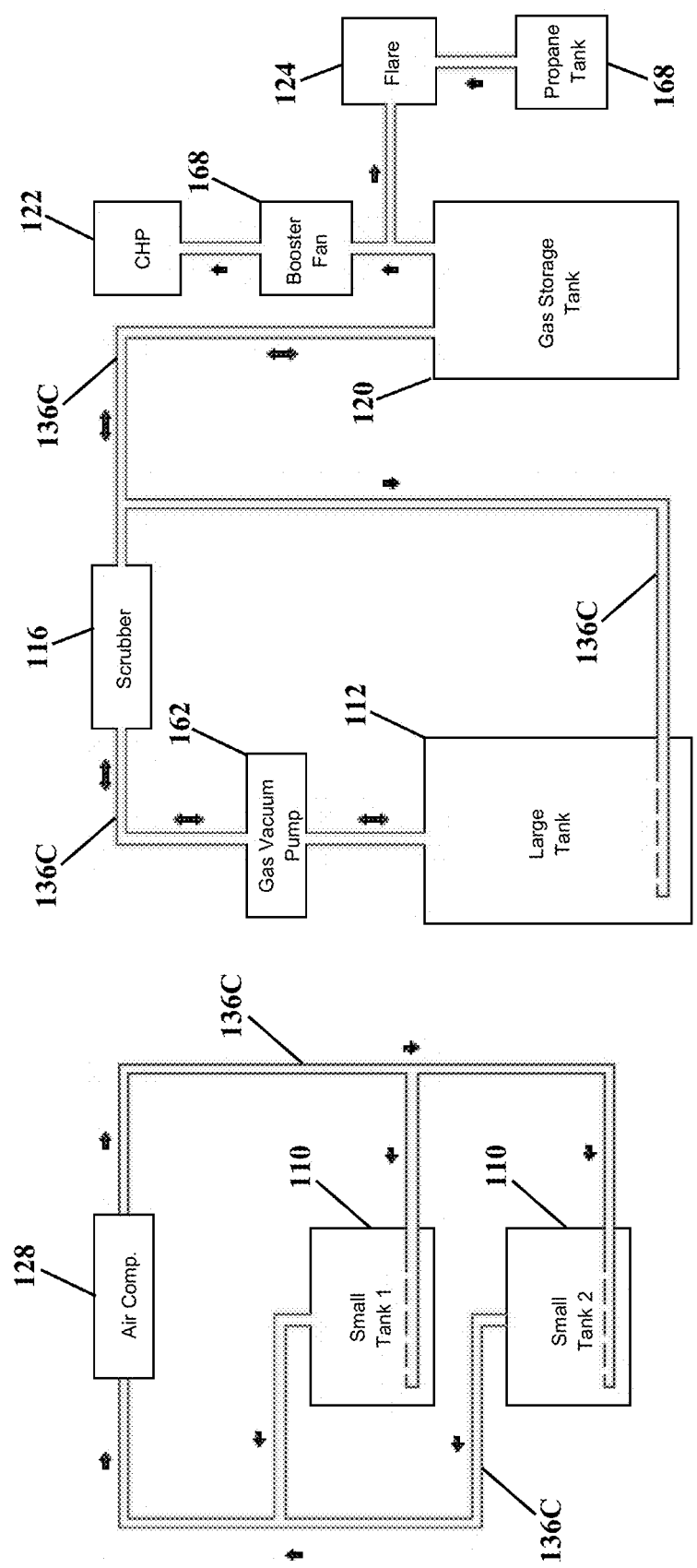
FIG. 7 is schematic diagram that illustrates gas piping according to a non-limiting embodiment of the present invention.

The gas piping 136C is preferably stainless steel due to the corrosive properties of elements within biogas. For example, there may be H$_2$S (Hydrogen Sulfide) in the biogas. Stainless steel piping does not react with that medium. And as FIG. 7 illustrates, the gas piping 136C forms two separate loops. The first loop circulates air through the small holding tanks 110 with the compressor 128 to stir the water/muck/waste in the small holding tanks 110. And the second loop circulates biogas through the large holding tank 112 with the gas vacuum pump 162 to stir the water/muck/waste in the large holding tank 112. The first loop is an "open" loop because it allows the introduction of air into the small holding tanks 110, and the second loop is a "closed" loop because it only utilizes the biogas already in the large holding tank 112.

The second loop also moves biogas from the large holding tank 112 to the gas storage tank 120 after scrubbing it with the gas scrubber 116. From the gas storage tank 120, the scrubbed biogas is moved to the biogas engine 122 using a booster fan 172 to maintain the biogas at the operating pressure required for the biogas engine 122. Any surplus biogas that cannot be stored by the gas storage tank 120 is safely burned off with the flare 124 so as to prevent unsafe levels of pressure occurring. And as discussed above, biogas may be circulated back into the large holding tank 112 to maintain the desired operating pressure therein during the draw down process. The ECU 118 controls the amounts of biogas moved between those components 112, 116, 120, and 122 as required to perform those operations by opening and closing the appropriate gas valves 134C and operating the gas vacuum pump 162 and the booster fan 172. And although FIG. 7 shows biogas being circulated back into the large holding tank through the gas scrubber 116, the gas scrubber 116 can be bypassed to perform that operation by opening and closing the appropriate gas valves 134C while the gas vacuum pump 162 is run in reverse. And although FIG. 7 shows two separate loops, those loops may be interconnected as required to recover biogas from the small holding tanks 110.

xiii. Odor Abatement System 908

To contend with the potentially bothersome odors generated by the anaerobic digestion process, the REM system 100 or 900 comprises an odor abatement system 908. The odor abatement system 908 receives atmosphere from the odor abatement pipeline 1006. The odor abatement system 908 then uses appropriate combination of odor abatement materials to filter out the odor to allow the atmosphere to be released without odor or need for a flare 124. The odor abatement materials are contained within special fabric bags that allow easy replacement. The odor abatement unit 908 is manufactured from appropriate materials that provide resistance to corrosion and erosion for 20 years. The bags with odor abatement material may require replacement at six month intervals as a maintenance item.

In another embodiment, the buffer tank 108, small holding tanks 110, de-watering unit 114, and liquor tank 126 may each include an exhaust stack 174 with a filter element. The filter element preferably utilizes organic filtering material, such as a combination of steel wool and ferns, to remove potentially bothersome odors from the gases generated in those components 108, 110, 114, and 126. And the exhaust stacks 174 preferably extend through the roof of the first container 102 so as to vent those gases outside of the first container 102. As discussed above, the large holding tank 112 does not include an exhaust stack 174 because the biogas generated therein is highly combustible. Accordingly, that biogas is either stored in the gas storage tank 120 or burned off by the flare 124. The exhaust stack 174 can be used in conjunction with the odor abatement system 908 to exhaust atmosphere when the odor abatement system is unable to process the excess atmosphere.

B. Method for Renewable Energy Microgeneration

The components 106-128 of the REM apparatus 100 are best described as forming separate nodes in the anaerobic digestion process. At node 1, the chopper unit 106 receives muck/waste (e.g., feedstocks) of variable solids contents that have to be diluted down to about 8-10% total solids and a ratio of about 1:4 of waste/muck to dilution liquid (e.g., potable or grey water). Dilution is achieved by adding the recycled grey water recovered from the fully digested water/muck/waste using the de-watering unit 114 at node 6. Potable water can also be added from an outside source as required, such as when the REM apparatus 100 is first commissioned. The ECU 118 controls the dilution process based on measurements obtained with level sensing equipment.

After the required amount of dilution liquid (e.g., potable and/or grey water) is added to the muck/waste in the mixing tank 202, the homogenizing pump 204 macerates the water/muck/waste mixture to obtain the desired viscosity. That process should take only a few minutes a day, after which, there should be a sufficient amount of homogenized water/muck/waste to begin pasteurization and digestion. The homogenizing pump 204 is preferably configured to process 0.5 metric tons of waste/muck an hour. And as discussed above, the REM apparatus 100 can be sized using modular components are required to process user-specific daily amounts of muck/waste.

At node 2, the water/muck/waste mixture produced at node 1 is transferred into the buffer tank 108 for pre-heating. The buffer tank 108 includes a heat exchanger 156 that cools the heated and partially pasteurized or digested water/muck/waste produced during pasteurization in the small holding tanks 110 at node 3 while warming the water/muck/waste mixture produced with at node 1. The heat energy lost by the heated and partially pasteurized or digested water/muck/ waste during cooling is transferred to the water/muck/waste mixture in the buffer tank 108 to warm it from its ambient temperature before it is moved to the small holding tanks 110. That process allows the water/muck/waste mixture going into the large digester to be at 35-40° C. so as to avoid thermal shock to mesophilic bugs in the large holding tank 112 at node 4. It also pre-heats the water/muck/waste mixture produced at node 1 so that less load is placed on the heaters 160 in the small holding tanks 110 at node 3, where the water/muck/waste mixture is heated to at least 70° C.

At node 3, the small holding tanks 110 use a gas mixer 158 to mix the water/muck/waste mixture with air, which allows bugs to use oxygen to heat up the water/muck/waste mixture during pasteurization. The contents of those small holding tanks 110 are also warmed with internal heaters 160 to an operating temperature of approximately 70° C. for a minimum of 60 minutes. That can be adjusted as required to optimize pasteurization using a SCADA system connected to the ECU 118 via the SCADA interface. Two or more small holding tanks 110 are preferably provided so that the bugs therein can be quickly and easily cycled through those tanks with feed, hold, and discharge steps. The feed and discharge steps would be more time consuming and difficult with larger tanks. Moreover, the load on the heaters 160 would be greater in larger tanks.

After pasteurization in the small holding tanks 110 is completed, the heated and partially pasteurized or digested water/muck/waste is moved to the large holding tank 112 for mesophilic anaerobic digestions and biogas recovery at nodes 4 and 5, respectively. As discussed above, that heated and partially pasteurized or digested water/muck/waste is cooled to 35-40° C. by the heat exchanger 156 in the buffer tank 108 at node 2 before it is deposited in the large holding tank 112 until a predetermined fill level is reached. In the large holding tank 112, the pasteurized or cooled and partially digested water/muck/waste is continuously stirred with the gas stirrer 158 by re-circulating the biogas generated during mesophilic anaerobic digestion back into the water/muck/waste. The feed flowrate to the large holding tank 112 is such that it provides a minimum retention time of 15 days. The temperatures and times at which the water/muck/waste is held in the small holding tanks 110 and large holding tank 112 is controlled by the ECU 118 so as to operate within the pertinent HACCPs and to comply with local, national, and/or international standards, such as U.S. EPA regulation 40 C.F.R. 503.32.

The biogas generated during mesophilic anaerobic digestion at node 4 is removed from the large holding tank 112 and placed in the gas storage tank 120 at node 5. That biogas is moved to the gas storage tank 120 by the gas vacuum pump 162 as it is being generated by the mesophilic anaerobic digestion. And after that process is complete, what remains of the water/muck/waste mixture is output to the de-watering unit 114 at node 6. As the large holding tank 112 is being drawn down in that manner, biogas is moved from the gas storage tank 120 back into the large holding tank 112 so as to maintain an operating pressure of 15-20 mbar in the large holding tank 112 during that draw-down process. Then, as the large holding tank 110 is being filled with the next batch of pasteurized or cooled and partially digested water/muck/waste at node 4, the biogas is moved back into the gas storage tank 120 at node 5.

At node 6, the fully digested water/muck/waste drawn from the large holding tanks 110 is pumped into the de-watering unit 114 for de-watering. The fully digested water/muck/waste undergoes pre-filtration by passing it through fine mesh to aid in the separation process. The fully digested water/muck/waste may also undergo desulfurization hydrogen sulfide scrubbing, or sweetening, in the de-watering tank 300. And coagulant may be added to aggregate suspended solids in the fully digested water/muck/waste so that they fall to the bottom of the de-watering tank 300, thereby leaving a top layer of cleaned "grey" water, or liquor, that is re-circulated back into the chopper unit 106 with the mixer feed pump 134B. The bacteria in the grey water can also be used as a feedstock, so it may also be gravity fed to the liquor tank 126 for storage at node 7.

The solids that fall to the bottom of the de-watering tank 300 form a thickened layer of organic fertilizer. The electric motor 304 of the de-watering unit 114 rotates the shaftless screw conveyor disposed within the conveyor tube 302 to transport that thickened layer of organic, solid fertilizer up through the conveyor tube 302 and out through the spout 306 disposed at the upper end of the conveyor tube 302, where it drops into a bin placed below the spout on the loading platform 142. The solid fertilizer, or mulch, collected in that bin is preferably 75 to 85% dry as a result of that process. And the resulting solid and liquid fertilizers produced by the digestion process will preferably be pathogen free. This fertilizer can be certified as pathogen free with storage or additional heating in compliance with prescribed regulations.

C. Modular Configurations

Although only two containers 102 and 104 are discussed with respect to the exemplary embodiments of the apparatus and method disclosed above, the components 106-128 of the REM apparatus 100 can be separated into as many different containers 102, 104, 1000, 1100, 1200, and 1300 as are required to suit the particular application. For example, a processing container (not depicted) could house the chopper unit 106, the buffer tank 108, the de-watering unit 114, and the ECU 118; a digestion container (not depicted) could house the small holding tanks 110, the large holding tank 112, and the gas scrubber 114; a CHP container (not depicted) could house the biogas engine 122; a liquor storage container (not depicted) could house one or more liquor storage tanks 126; and a gas storage container 104 could house one or more gas storage tanks 120. In that configuration, the processing container would process all of the muck/waste and water/muck/waste before and after the anaerobic digestion process; the digestion container would perform the pasteurization or thermophilic anaerobic digestion, the mesophilic anaerobic digestion, and the biogas scrubbing; and the gas storage container would perform all of the biogas storage. One or more digestions containers could thereby be added to the processing container and gas storage container until the processing capacity of processing container and/or the storage capacity of the gas storage container was reached. Accordingly, those containers are preferably interconnected using standardized piping 136A-136C and wiring 138 (e.g., prefabricated piping sections and wiring harnesses) to allow them to be connected in a modular manner, thereby allowing expansion of the REM apparatus 100 to suit substantially any throughout requirement.

By way of more specific example, if the chopper unit 106 in each processing container can process 0.5 metric tons of waste/muck an hour, a user that wants to process 6 metric tons of waste/muck in a 8-hour day could obtain two processing containers and configure them to operate in unison, thereby allowing that user to process that amount of waste/muck over a 6-hour period. Similarly, two processing containers could be provided to process 24 metric tons of waste/muck in a 24-hour period. Those two processing containers could then be connected to a corresponding number of digestion containers in a daisy chain configuration using the aforementioned standardized piping 136A-136C and wiring 138.

Figure 8:
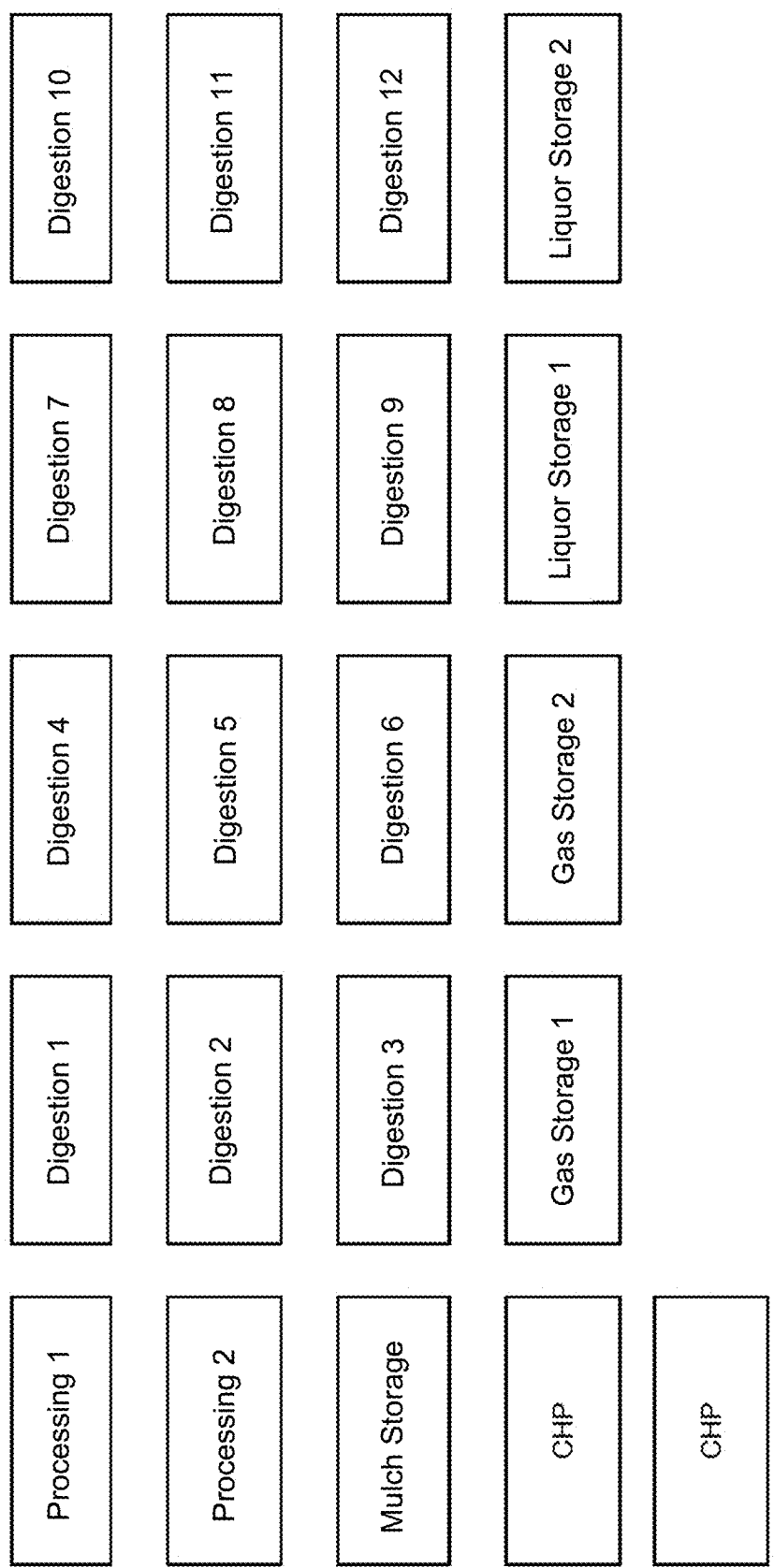
FIG. 8 is schematic diagram that illustrates a 6-ton per day configuration of the present invention.

Because the anaerobic digestion process typically requires a ratio of about 1:4 of waste/muck to dilution liquid (e.g., potable and/or grey water), processing 6 metric tons of waste/muck a day will produce approximately 30 tons of water/waste/muck mixture (6 metric tons waste/mulch+(4× 6) metric tons dilution liquid=30 metric tons water/waste/muck mixture). And, because the digestion process in the large holding tanks 110 will take approximately twenty-one days, approximately 630 metric tons (~630 m³) of storage will be required to allow a continuous cycle of waste/muck to be processed at a rate of 6 metric tons per day (30 metric tons/day×21 days/digestion cycle=630 metric tons/digestion cycle). Thus, twelve digestion containers, each having four 1,800 Liter small holding tanks and two 14,000 Liter large digestion tanks 112, would be needed to digest 30 metric tons of water/waste/muck mixture in that 21-day period, as illustrated in FIG. 8.

That 6-ton per day solution is estimated to create 600 m³ of biogas at 55-60 percent methane. In such a large capacity process, two gas storage containers would need to be provided to store that biogas and at least two CHP containers would need to be provided to convert that biogas into heat and/or electricity, as also illustrated in FIG. 8. Preferably, at least three biogas engines 122 will be provide between those two CHP containers so that two biogas engines 122 can be used to burn the biogas and the third can be used as a back-up.

Also in that 6-ton per day configuration, two liquor storage containers would be needed to store the grey water removed from the fully digested water/muck/waste after anaerobic digestion is complete. A mulch storage container may also be provided for storing the solid fertilizer generated from the fully digested water/muck/waste after the grey water is removed. Those additional containers are also illustrated in FIG. 8.

Each of the processing containers, digestion containers, CHP containers, liquor storage containers, gas storage containers, and mulch storage containers discussed above is preferably a standard 20-foot container. If a larger capacity of processing is required, 40-foot containers may also be used. And, if 40-foot containers are not suitable, modular custom containers can be used to suite the required capacity. Those custom containers can be assembled on site from pre-formed insulated concrete or metal panels. The custom containers can be erected on a concrete slab that is poured on site by wiring or bolting the pre-formed panels together. The custom containers can be squared, can have rounded edges, can have a domed roof, or any other suitable configuration.

The large holding tanks 112 can be formed in a substantially similar manner if required. By way of example, if 24 metric tons of waste/muck is desired to be processed in a day, two processing containers can be provided with three custom large holding tanks 112 formed as described above—two for storing the water/waste/muck mixture during the digestion process and one for holding that mixture if/when a problem occurs with one of the other large holding tanks.

By making the processing containers, digestion containers, CHP containers, liquor containers, gas storage containers, and mulch storage containers of the present invention modular, an REM apparatus 100 can be put together from those containers to suit substantially any application. Thus, instead of having to build a new and different waste treatment plant for every application, the REM apparatus 100 of the present invention can be sized to suit. Moreover, by separating the components 106-114 in the processing containers and the biogas engines 122 in the CHP containers from the small holding tanks 110, large holding tanks 112, and gas storage tanks 120, the potential danger of accidentally igniting the biogas generated and/or stored in those tanks is avoided.

SUMMARY

In summary, the present invention provides a novel solution to waste disposal problems while providing a sustainable source of energy. After the present invention is installed, all the user needs to do is load his or her waste into the apparatus and the system will process the waste to produce heat, biogas, electricity, and fertilizer. And after only a few weeks of use, the user will have a continuous supply of electricity. The present invention provides at least the following advantages: 1) it generates electricity from horse muck year round; 2) it converts septic waste into hot water and/or heat; 3) it eliminates the cost of disposal, unsightly muck heaps, and smelly septic systems; and 4) it generates useful bi-products, including solid and liquid fertilizers.

The REM apparatus 100 is an automated plant that requires no intervention except daily feeding with muck/waste. The embodiment of FIGS. 1A-1E is capable of processing 400 kg of muck/waste (e.g., feedstock) per day, which is digested over 15 days to produce about 2,000 Liters of biogas and a pasteurized mulch product that meets or exceeds the PAS 110 quality protocol. The grey water, or liquor, also meets or exceeds that quality protocol. The REM apparatus 100 is also designed to process muck/waste at temperatures and times within the pertinent HACCPs and that comply with U.S. EPA regulations (e.g., 40 C.F.R. 503.32). As discussed above, the ECU 118 is programmed to control those temperatures and times. And proper separation of components 106-128 is provided as required to comply with the European Union's ATEX directive and DSEARs.

The apparatus and method of the present invention are particularly suited for processing waste/much such as organic and septic waste, including but not limited to various types of farm animal manure (e.g., horse, cow, pig, and chicken manure); meat, blood, and other slaughterhouse waste; garden and agricultural green waste; food preparation and kitchen waste; wasted/leftover/spoiled food; and septic tank contents. That muck/waste is digested with a mix of bacteria in an anaerobic digestion process to produce biogas (e.g., methane and carbon dioxide), and what remains of the muck/waste after that process is separated into a dry mulch and a liquid fertilizer. The biogas can be combusted in a CHP unit to generate heat and electrical power; the mulch can be used as animal bedding; and the liquid fertilizer can be used to put back into the soil to increase its nutrient content and fertility. Moreover, excess electricity generated with the CHP can be sold back to the national grid.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. For example, the mixers 138 may comprise rotational mechanical stirring devices rather than air nozzles and the biogas engine 122 may be a biogas generator rather than a CHP. Therefore, it is not desired to limit the invention to the specific examples disclosed or the exact construction and operation shown and described. Rather, all suitable modifications and equivalents may be resorted to, falling within the scope of the invention.

What is claimed is:

1. A portable and modular renewable energy microgeneration apparatus comprising:
a first modular unit comprising:
a mixing tank that is configured to mix incoming waste with a liquid, and
a chopper in fluid communication with the mixing tank that is configured to reduce the waste to smaller sized components;
a second modular unit comprising:
a buffer tank that is configured to receive the waste from the mixing tank and pre-warm the waste in preparation for pasteurization,
a liquor tank configured to receive liquid removed from a digestion tank, the liquid received by the liquor tank being received for mixing with the waste in the first modular unit, and
a pasteurization tank that is configured to perform pasteurization on waste received from the buffer tank;
a third modular unit comprising the digestion tank, which is configured to perform anaerobic digestion on waste received from the pasteurization tank;
a fourth modular unit comprising a gas storage tank that is configured to store gas generated by the waste in at least one of the mixing tank, the chopper, the buffer tank, the liquor tank, the pasteurization tank, and the digestion tank;
a de-watering device that is configured to separate liquid digestate and to remove salt from the liquid separated from the liquid digestate;
first sensors disposed in the buffer tank and the digestion tank that are configured to measure salinity; and
a controller that is configured to:
cause a transfer of digestate from the digestion tank to the pasteurization tank after anaerobic digestion of the waste occurs,
cause a transfer of digestate from the pasteurization tank to the dewatering device after the digestate received from the digestion tank is pasteurized,
cause the de-watering device to separate liquid from the digestate received from the pasteurization tank and to remove salt from the liquid separated from the digestate to create a liquid with a reduced salinity,
monitor the salinity of liquid in the buffer tank and the digestion tank using the first sensors, and
cause a mixing of the liquid with the reduced salinity with the waste and adjust a feed rate of the waste to the digestion tank as required to reduce the salinity of the waste,
wherein the first modular unit, the second modular unit, the third modular unit, and the fourth modular unit are portable in that they are configured to be transported to a site and paced in fluid communication with each other at the site, and
wherein the first modular unit, the second modular unit, the third modular unit, and the fourth modular unit are modular in that they can be combined with each other in different numbers and configurations.

2. A portable and modular renewable energy microgeneration apparatus comprising:
a first modular unit comprising:
a mixing tank that is configured to mix incoming waste with a liquid, and
a chopper in fluid communication with the mixing tank that is configured to reduce the waste to smaller sized components;
a second modular unit comprising:
a buffer tank that is configured to receive the waste from the mixing tank and pre-warm the waste in preparation for pasteurization,
a liquor tank configured to receive liquid removed from a digestion tank, the liquid received by the liquor tank being received for mixing with the waste in the first modular unit, and
a pasteurization tank that is configured to perform pasteurization on waste received from the buffer tank;
a third modular unit comprising the digestion tank, which is configured to perform anaerobic digestion on waste received from the pasteurization tank;
a fourth modular unit comprising a gas storage tank that is configured to store gas generated by the waste in at least one of the mixing tank, the chopper, the buffer tank, the liquor tank, the pasteurization tank, and the digestion tank; and
a $CO_2$ extraction system configured to:
separate $CO_2$ from the gas generated by the waste in at least one of the mixing tank, the chopper, the buffer tank, the liquor tank, the pasteurization tank, and the digestion tank; and
inject the $CO_2$ into the digestion tank to stir the waste in the second holding tank,
wherein the first modular unit, the second modular unit, the third modular unit, and the fourth modular unit are portable in that they are configured to be transported to a site and placed in fluid communication with each other at the site, and
wherein the first modular unit, the second modular unit, the third modular unit, and the fourth modular unit are modular in that they can be combined with each other in different numbers and configurations.

3. A portable and modular renewable energy microgeneration apparatus comprising
a first modular unit comprising:
a mixing tank that is configured to mix incoming waste with a liquid, and
a chopper in fluid communication with the mixing tank that is configured to reduce the waste to smaller sized components;
a second modular unit comprising:
a buffer tank that is configured to receive the waste from the mixing tank and pre-warm the waste in preparation for pasteurization,
a liquor tank configured to receive liquid removed from a digestion tank, the liquid received by the liquor tank being received for mixing with the waste in the first modular unit, and
a pasteurization tank that is configured to perform pasteurization on waste received from the buffer tank;
a third modular unit comprising the digestion tank, which is configured to perform anaerobic digestion on waste received from the pasteurization tank;
a fourth modular unit comprising a gas storage tank that is configured to store gas generated by the waste in at least one of the mixing tank, the chopper, the buffer tank, the liquor tank, the pasteurization tank, and the digestion tank; and a fifth modular unit, wherein the fifth modular unit comprises a de-watering device that is configured to separate liquid digestate and to remove salt from the liquid separated from the liquid digestate;

wherein the first modular unit, the second modular unit, the third modular unit, the fourth modular unit, and the fifth modular unit are portable in that they are configured to be transported to a site and placed in fluid communication with each other at the site, and wherein the first modular unit, the second modular unit, the third modular unit, the fourth modular unit, and the fifth modular unit are modular in that they can be combined with each other in different numbers and configurations.

4. The apparatus of claim 3, wherein the apparatus further comprises a containerizing system configured to place solid waste output by the de-watering device into standard sized containers.

5. A portable and modular renewable energy microgeneration apparatus comprising:
a first modular unit comprising:
a mixing tank that is configured to mix incoming waste with a liquid, and
a chopper in fluid communication with the mixing tank that is configured to reduce the waste to smaller sized components;
a second modular unit comprising:
a buffer tank that is configured to receive the waste from the mixing tank and pre-warm the waste in preparation for pasteurization,
a liquor tank configured to receive liquid removed from a digestion tank, the liquid received by the liquor tank being received for mixing with the waste in the first modular unit, and
a pasteurization tank that is configured to perform pasteurization on waste received from the buffer tank;
a third modular unit comprising the digestion tank, which is configured to perform anaerobic digestion on waste received from the pasteurization tank;
a fourth modular unit comprising a gas storage tank that is configured to store gas generated by the waste in at least one of the mixing tank, the chopper, the buffer tank, the liquor tank, the pasteurization tank, and the digestion tank; and
an odor management system configured to:
remove gas from within at least one of the first modular unit, the second modular unit, and the third modular unit;
filter odors from the gas removed from the at least one of the first modular unit, the second modular unit, and the third modular unit; and
vent to atmosphere the gas removed from the at least one of the first modular unit, the second modular unit, and the third modular unit,
wherein the gas removed from the at least one of the first modular unit, the second modular unit, and the third modular unit differs from the gas generated by the waste in at least one of the mixing tank, the chopper, the buffer tank, the liquor tank, the pasteurization tank, the digestion tank, and the gas storage tank,
wherein the first modular unit, the second modular unit, the third modular unit, and the fourth modular unit are portable in that they are configured to be transported to a site and placed in fluid communication with each other at the site, and wherein the first modular unit, the second modular unit, the third modular unit, and the fourth modular unit are modular in that they can be combined with each other in different numbers and configurations.

6. A portable and modular renewable energy microgeneration apparatus comprising:
a first modular unit comprising:
a mixing tank that is configured to mix incoming waste with a liquid, and
a chopper in fluid communication with the mixing tank that is configured to reduce the waste to smaller sized components;
a second modular unit comprising:
a buffer tank that is configured to receive the waste from the mixing tank and pre-warm the waste in preparation for pasteurization,
a liquor tank configured to receive liquid removed from a digestion tank, the liquid received by the liquor tank being received for mixing with the waste in the first modular unit, and
a pasteurization tank that is configured to perform pasteurization on waste received from the buffer tank;
a third modular unit comprising the digestion tank, which is configured to perform anaerobic digestion on waste received from the pasteurization tank;
a fourth modular unit comprising a gas storage tank that is configured to store gas generated by the waste in at least one of the mixing tank, the chopper, the buffer tank, the liquor tank, the pasteurization tank, and the digestion tank,
wherein the first modular unit, the second modular unit, the third modular unit, and the fourth modular unit are portable in that they are configured to be transported to a site and placed in fluid communication with each other at the site,
wherein the first modular unit, the second modular unit, the third modular unit, and the fourth modular unit are modular in that they can be combined with each other in different numbers and configurations,
wherein each of the first modular unit, the second modular unit, the third modular unit, and the fourth modular unit is disposed in a portable container; and
wherein each portable container is configured to withstand explosions of a predetermined magnitude without compromising an adjacent container.

7. The apparatus of claim 6, further comprising a natural gas boiler configured to generate at least one of electricity and heat from the gas stored in the gas storage tank.

8. The apparatus of claim 6, wherein the apparatus comprises a plurality of first modular units and each of the plurality of first modular units is configured to receive different types of waste.

9. The apparatus of claim 6, wherein each of the first modular unit, the second modular unit, the third modular unit, and the fourth modular unit is housed in a stackable container so that the first modular unit, the second modular unit, the third modular unit, and the fourth modular unit may be stacked one on top of the other in different configurations.

10. A portable and modular renewable energy microgeneration apparatus comprising:
a first modular unit comprising:
a mixing tank that is configured to mix incoming waste with a liquid, and a chopper in fluid communication with the mixing tank that is configured to reduce the waste to smaller sized components;

a second modular unit comprising:
- a buffer tank that is configured to receive the waste from the mixing tank and pre-warm the waste in preparation for pasteurization,
- a liquor tank configured to receive liquid removed from a digestion tank, the liquid received by the liquor tank being received for mixing with the waste in the first modular unit, and
- a pasteurization tank that is configured to perform pasteurization on waste received from the buffer tank;

a third modular unit comprising the digestion tank, which is configured to perform anaerobic digestion on waste received from the pasteurization tank;

a fourth modular unit comprising a gas storage tank that is configured to store gas generated by the waste in at least one of the mixing tank, the chopper, the buffer tank, the liquor tank, the pasteurization tank, and the digestion tank, wherein the first modular unit, the second modular unit, the third modular unit, and the fourth modular unit are portable in that they are configured to be transported to a site and placed in fluid communication with each other at the site, wherein the first modular unit, the second modular unit, the third modular unit, and the fourth modular unit are modular in that they can be combined with each other in different numbers and configurations, wherein each of the first modular unit, the second modular unit, the third modular unit, and the fourth modular unit is disposed in a container;

wherein the first modular unit, the second modular unit, the third modular unit, and the fourth modular unit are configured to be combined with each other in different numbers and configurations using piping and wiring disposed within the container of each of the first modular unit, the second modular unit, the third modular unit, and the fourth modular unit; and wherein the piping and wiring are configured to be connected and disconnected via connection points housed within the container of each of the first modular unit, the second modular unit, the third modular unit, and the fourth modular unit.

* * * * *